United States Patent
Kiriyama et al.

(10) Patent No.: US 9,688,634 B2
(45) Date of Patent: Jun. 27, 2017

(54) PEST CONTROL AGENT

(71) Applicant: ISHIHARA SANGYO KAISHA, LTD., Osaka (JP)

(72) Inventors: Kazuhisa Kiriyama, Kusatsu (JP); Masahiro Matsumoto, Kusatsu (JP); Kotaro Yoshida, Kusatsu (JP); DamdinSuren Boldbaatar, Kusatsu (JP); Tatsuya Jukurogi, Kusatsu (JP); Nao Umemoto, Kusatsu (JP); Tatsuya Kani, Kusatsu (JP); Yoko Matsuda, Kusatsu (JP); Kumiko Tanaka, Kusatsu (JP); Michiko Kanuma, Kusatsu (JP); Tatsuya Shimada, Kusatsu (JP)

(73) Assignee: ISHIHARA SANGYO KAISHA, LTD., Osaka (JP)

( * ) Notice: Subject to any disclaimer, the term of this patent is extended or adjusted under 35 U.S.C. 154(b) by 0 days.

(21) Appl. No.: 14/653,059

(22) PCT Filed: Dec. 19, 2013

(86) PCT No.: PCT/JP2013/085022
§ 371 (c)(1),
(2) Date: Jun. 17, 2015

(87) PCT Pub. No.: WO2014/098259
PCT Pub. Date: Jun. 26, 2014

(65) Prior Publication Data
US 2015/0336894 A1    Nov. 26, 2015

(30) Foreign Application Priority Data

Dec. 21, 2012 (JP) ................................ 2012-280207
Aug. 6, 2013  (JP) ................................ 2013-162860
Oct. 10, 2013 (JP) ................................ 2013-212795

(51) Int. Cl.
| | |
|---|---|
| C07D 213/16 | (2006.01) |
| C07D 401/06 | (2006.01) |
| A01N 43/40 | (2006.01) |
| C07D 213/72 | (2006.01) |
| C07D 213/73 | (2006.01) |
| C07D 213/74 | (2006.01) |
| C07D 213/75 | (2006.01) |
| C07D 213/24 | (2006.01) |
| C07D 213/60 | (2006.01) |
| C07D 213/61 | (2006.01) |
| C07D 213/62 | (2006.01) |
| C07D 213/70 | (2006.01) |

(52) U.S. Cl.
CPC .......... *C07D 213/16* (2013.01); *A01N 43/40* (2013.01); *C07D 213/24* (2013.01); *C07D 213/60* (2013.01); *C07D 213/61* (2013.01); *C07D 213/62* (2013.01); *C07D 213/70* (2013.01); *C07D 213/72* (2013.01); *C07D 213/73* (2013.01); *C07D 213/74* (2013.01); *C07D 213/75* (2013.01); *C07D 401/06* (2013.01)

(58) Field of Classification Search
None
See application file for complete search history.

(56) References Cited

U.S. PATENT DOCUMENTS

| | | | |
|---|---|---|---|
| 5,013,744 A | 5/1991 | Chandraratna | |
| 6,340,759 B1 * | 1/2002 | Ueno ................... | C07D 217/22 544/358 |

FOREIGN PATENT DOCUMENTS

| | | |
|---|---|---|
| CN | 104045552 A | 9/2014 |
| JP | 61-60638 A | 3/1986 |
| JP | 61060638 * | 3/1986 |
| JP | 01-316359 A | 12/1989 |
| JP | 2010-222551 A | 10/2010 |
| WO | 94/22833 A1 | 10/1994 |
| WO | 96/33975 A1 | 10/1996 |
| WO | 2010/064711 A1 | 6/2010 |
| WO | 2010/115901 A1 | 10/2010 |
| WO | WO2010/115901 * | 10/2010 |
| WO | 2011/103225 A1 | 8/2011 |
| WO | 2012/008526 A1 | 1/2012 |
| WO | 2013/024009 A1 | 2/2013 |

OTHER PUBLICATIONS

Ziegler et al., 6(3) Chimica Therapeutica 159-66 (1971) (CAS Abstract).*
Rustagi et al., 13(7) Green Chem. 1640-1643 (2011) (CAS Abstract).*
Ziegler, H J, et al., "Recherches dans la serie des benzofurannes. XXXIII.—Nouvelles methodes de synthase de benzofurannes basiques: en particulier de (pyridyl)-2 benzofurannes et d¹(aminoalkyl)-2 benzofurannes doues de proprietes neurodepressives [Benzofurans. XXXIII. New methods of preparing basic benzofurans. Neuro", Chimie Therapeutique, Editions Dimeo, Arcueil, FR, vol. 6, No. 3, Jan. 1, 1971 (Jan. 1, 1971), pp. 159-166.
International Search Report for PCT/JP2013/085022 dated Mar. 28, 2014 [PCT/ISA/210].
Written Opinion for PCT/JP2013/085022 dated Mar. 28, 2014 [PCT/ISA/237].
Opposition served on Feb. 1, 2016 by the Costa Rican Patent Office in related Application No. 2015-0328.

* cited by examiner

*Primary Examiner* — Timothy R Rozof
(74) *Attorney, Agent, or Firm* — Sughrue Mion, PLLC

(57) ABSTRACT

Objects of the present invention are to provide a compound which is highly active against pests, to provide a pest control agent comprising the compound, and to provide a method for controlling a pest by applying the compound. The present invention provides a 4-(arylethynyl)pyridine or a salt thereof, a pest control agent which comprises the 4-(arylethynyl)pyridine or salt thereof as an active ingredient, and a method for controlling a pest by applying the 4-(arylethynyl)pyridine or salt thereof in an effective amount.

7 Claims, No Drawings

PEST CONTROL AGENT

TECHNICAL FIELD

The present invention relates to a pest control agent which comprises a novel 4-(arylethynyl)pyridine compound or a salt thereof as an active ingredient.

BACKGROUND ART

PLT 1 discloses that a specific 4-(aryl)pyridine derivative is useful as an agricultural or horticultural insecticide, and PLT 2 discloses that a specific pyridine compound is effective in controlling pests. Furthermore, PLT 3 describes a pyridine derivative and a salt thereof which have an insecticidal and miticidal action. However, PLTs 1, 2, and 3 include no description at all concerning the compound of the present invention. PLT 4, which relates to a pyrrolopyridine compound for a therapeutic agent for hepatitis virus, discloses a given 4-(arylethynyl)pyridine derivative in a scheme for synthesizing the compound.

CITATION LIST

Patent Literature

[PLT 1]: WO 2010/064711
[PLT 2]: WO 2012/008526
[PLT 3]: JP-A-1-316359
[PLT 4]: WO 2010/115901

SUMMARY OF INVENTION

Technical Problem

Although a large number of pest control agents have been in use for many years, not a few of these have various problems, for example, that the effect is insufficient and that the pests or the like have acquired resistance and the use thereof is limited. It is hence desired to develop a novel pest control agent in which such drawbacks have been mitigated. Objects of the present invention are to provide a compound which is highly active against pests, to provide a pest control agent which comprises the compound, and to provide a method for controlling a pest by applying the compound.

Solution to Problem

The present inventors made investigations on various pyridine derivatives in order to find out an even better pest control agent. As a result, the inventors have found that a novel 4-(arylethynyl)pyridine compound is exceedingly highly effective in controlling pests when applied in a small dose. The present invention has been thus completed.

That is, the present invention is summarized in the following (1) to (8).
(1) A compound represented by general formula (I):

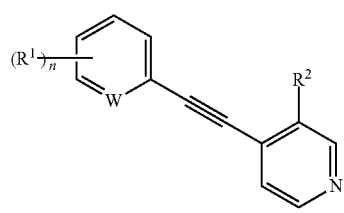

[wherein
$R^1$ is a halogen atom, an amino group, a hydroxyl group, a mercapto group, a cyano group, a nitro group, a $(C_1-C_6)$alkyl group, a $(C_2-C_6)$alkenyl group, a $(C_2-C_6)$alkynyl group, a $(C_3-C_6)$cycloalkyl group, a $(C_1-C_6)$haloalkyl group, a $(C_1-C_6)$alkoxy group, a $(C_2-C_6)$alkenyloxy group, a $(C_2-C_6)$alkynyloxy group, a $(C_3-C_6)$cycloalkoxy group, a $(C_1-C_6)$haloalkoxy group, a $(C_1-C_6)$alkylthio group, a $(C_2-C_6)$alkenylthio group, a $(C_2-C_6)$alkynylthio group, a $(C_3-C_6)$cycloalkylthio group, a $(C_1-C_6)$haloalkylthio group, a $(C_1-C_6)$alkylamino group, a $(C_2-C_6)$alkenylamino group, a $(C_2-C_6)$alkynylamino group, a di$(C_1-C_6)$alkylamino group, a di$(C_2-C_6)$alkenylamino group, a di$(C_2-C_6)$alkynylamino group, a $(C_1-C_6)$alkylsulfinyl group, a $(C_2-C_6)$alkenylsulfinyl group, a $(C_2-C_6)$alkynylsulfinyl group, a $(C_3-C_6)$cycloalkylsulfinyl group, a $(C_1-C_6)$haloalkylsulfinyl group, a $(C_1-C_6)$alkylsulfonyl group, a $(C_2-C_6)$alkenylsulfonyl group, a $(C_2-C_6)$alkynylsulfonyl group, a carboxyl group, a $(C_1-C_6)$alkylcarbonyl group, a $(C_1-C_6)$alkoxycarbonyl group, a $(C_1-C_6)$alkylaminocarbonyl group, a di$(C_1-C_6)$alkylaminocarbonyl group, a $(C_1-C_6)$alkylcarbonyloxy group, a $(C_1-C_6)$alkylcarbonylamino group, or a $(C_1-C_6)$alkylcarbonyl$(C_1-C_6)$alkylamino group;
$R^2$ is a halogen atom, an amino group, a hydroxyl group, a mercapto group, a cyano group, a nitro group, a $(C_1-C_6)$alkyl group, a $(C_2-C_6)$alkenyl group, a $(C_2-C_6)$alkynyl group, a $(C_1-C_6)$haloalkyl group, a $(C_1-C_6)$alkoxy group, a $(C_2-C_6)$alkenyloxy group, a $(C_2-C_6)$alkynyloxy group, a $(C_1-C_6)$alkylthio group, a $(C_2-C_6)$alkenylthio group, a $(C_2-C_6)$alkynylthio group, a $(C_1-C_6)$alkylamino group, a $(C_2-C_6)$alkenylamino group, a $(C_2-C_6)$alkynylamino group, a di$(C_1-C_6)$alkylamino group, a di$(C_2-C_6)$alkenylamino group, a di$(C_2-C_6)$alkynylamino group, a $(C_1-C_6)$alkylsulfinyl group, a $(C_2-C_6)$alkenylsulfinyl group, a $(C_2-C_6)$alkynylsulfinyl group, a $(C_1-C_6)$alkylsulfonyl group, a $(C_2-C_6)$alkenylsulfonyl group, a $(C_2-C_6)$alkynylsulfonyl group, a $(C_1-C_6)$alkyloxy$(C_1-C_6)$alkyl group, a $(C_1-C_6)$alkylthio$(C_1-C_6)$alkyl group, a $(C_1-C_6)$alkylamino$(C_1-C_6)$alkyl group, a di$(C_1-C_6)$alkylamino$(C_1-C_6)$alkyl group, a hydroxyl$(C_1-C_6)$alkyl group, a formyl group, a carboxyl group, a $(C_1-C_6)$alkylcarbonyl group, a $(C_1-C_6)$alkoxycarbonyl group, a $(C_1-C_6)$alkylaminocarbonyl group, a di$(C_1-C_6)$alkylaminocarbonyl group, a $(C_1-C_6)$alkylcarbonyloxy group, a $(C_1-C_6)$alkylcarbonylthio group, a $(C_1-C_6)$alkylcarbonylamino group, or a di$(C_1-C_6)$alkylcarbonylamino group; W is CH or a nitrogen atom; n is an integer of 1-4; and when n is 2 or larger, the $R^1$ moieties may be the same or different] or a salt thereof.
(2) The compound represented by general formula (I):

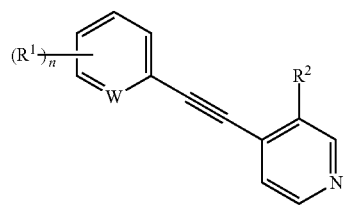

[wherein
$R^1$ is a halogen atom, an amino group, a hydroxyl group, a mercapto group, a cyano group, a nitro group, a $(C_1-C_6)$alkyl group, a $(C_2-C_6)$alkenyl group, a $(C_2-C_6)$alkynyl group, a $(C_3-C_6)$cycloalkyl group, a $(C_1-C_6)$haloalkyl group, a $(C_1-C_6)$alkoxy group, a $(C_2-C_6)$alkenyloxy group, a $(C_2-C_6)$ alkynyloxy group, a ($C_3$-$C_6$)cycloalkoxy group, a ($C_1$-$C_6$) haloalkoxy group, a ($C_1$-$C_6$)alkylthio group, a ($C_2$-$C_6$) alkenylthio group, a ($C_2$-$C_6$)alkynylthio group, a ($C_3$-$C_6$) cycloalkylthio group, a ($C_1$-$C_6$)haloalkylthio group, a ($C_1$-$C_6$)alkylamino group, a ($C_2$-$C_6$)alkenylamino group, a ($C_2$-$C_6$)alkynylamino group, a di($C_1$-$C_6$)alkylamino group, a di($C_2$-$C_6$)alkenylamino group, a di($C_2$-$C_6$)alkynylamino group, a ($C_1$-$C_6$)alkylsulfinyl group, a ($C_2$-$C_6$)alkenylsulfinyl group, a ($C_2$-$C_6$)alkynylsulfinyl group, a ($C_3$-$C_6$)cycloalkylsulfinyl group, a ($C_1$-$C_6$)haloalkylsulfinyl group, a ($C_1$-$C_6$)alkylsulfonyl group, a ($C_2$-$C_6$)alkenylsulfonyl group, a ($C_2$-$C_6$)alkynylsulfonyl group, a carboxyl group, a ($C_1$-$C_6$)alkylcarbonyl group, a ($C_1$-$C_6$)alkoxycarbonyl group, a ($C_1$-$C_6$)alkylaminocarbonyl group, a di($C_1$-$C_6$)alkylaminocarbonyl group, a ($C_1$-$C_6$)alkylcarbonyloxy group, a ($C_1$-$C_6$)alkylcarbonylamino group, or a ($C_1$-$C_6$) alkylcarbonyl($C_1$-$C_6$)alkylamino group;
$R^2$ is a halogen atom, a hydroxyl group, a mercapto group, a nitro group, a ($C_1$-$C_6$)alkyl group, a ($C_2$-$C_6$)alkenyl group, a ($C_2$-$C_6$)alkynyl group, a ($C_1$-$C_6$)haloalkyl group, a ($C_r$-$C_6$)alkoxy group, a ($C_2$-$C_6$)alkenyloxy group, a ($C_2$-$C_6$) alkynyloxy group, a ($C_1$-$C_6$)alkylthio group, a ($C_2$-$C_6$)alkenylthio group, a ($C_2$-$C_6$)alkynylthio group, a ($C_1$-$C_6$)alkylamino group, a ($C_2$-$C_6$)alkenylamino group, a ($C_2$-$C_6$) alkynylamino group, a di($C_1$-$C_6$)alkylamino group, a di($C_2$-$C_6$)alkenylamino group, a di($C_2$-$C_6$)alkynylamino group, a ($C_1$-$C_6$)alkylsulfinyl group, a ($C_2$-$C_6$)alkenylsulfinyl group, a ($C_2$-$C_6$)alkynylsulfinyl group, a ($C_1$-$C_6$)alkylsulfonyl group, a ($C_2$-$C_6$)alkenylsulfonyl group, a ($C_2$-$C_6$)alkynylsulfonyl group, a ($C_1$-$C_6$)alkyloxy($C_1$-$C_6$)alkyl group, a ($C_1$-$C_6$)alkylthio($C_1$-$C_6$)alkyl group, a ($C_1$-$C_6$)alkylamino($C_1$-$C_6$)alkyl group, a di($C_1$-$C_6$)alkylamino($C_1$-$C_6$)alkyl group, a hydroxyl($C_1$-$C_6$)alkyl group, a carboxyl group, a ($C_1$-$C_6$)alkylcarbonyl group, a ($C_1$-$C_6$)alkylaminocarbonyl group, a di($C_r$-$C_6$)alkylaminocarbonyl group, a ($C_1$-$C_6$) alkylcarbonyloxy group, a ($C_1$-$C_6$)alkylcarbonylthio group, a ($C_1$-$C_6$)alkylcarbonylamino group, or a di($C_1$-$C_6$)alkylcarbonylamino group; W is CH or a nitrogen atom; n is an integer of 1-4; when n is 2 or larger, the $R^1$ moieties may be the same or different; and when $R^2$ is a ($C_1$-$C_6$)alkyl group, no $R^1$ moiety substitutes at the ortho position] or a salt thereof according to (1).
(3) A pest control agent which comprises the compound or salt thereof according to (1) as an active ingredient.
(4) A pest control agent for agricultural or horticultural use which comprises the compound or salt thereof according to (1) as an active ingredient.
(5) An insecticide, miticide, nematicide, or soil pesticide which comprises the compound or salt thereof according to (1) as an active ingredient.
(6) An insecticide or miticide which comprises the compound or salt thereof according to (1) as an active ingredient.
(7) An agent for killing animal parasites, comprising the compound or salt thereof according to (1) as an active ingredient.
(8) A method for controlling a pest, comprising applying the compound or salt thereof according to (1) in an effective amount.

Advantageous Effects of Invention

The pest control agent comprising a compound of a general formula (I) or a salt thereof as an active ingredient is exceedingly highly effective in controlling pests when applied in a small dose.

DESCRIPTION OF EMBODIMENTS

Examples of the halogen atoms in general formula (I) or of the halogens as the substituents therein may include the atom of fluorine, chlorine, bromine, or iodine. The number of halogen atoms as the substituent(s) may be 1 or more. In the case where the number thereof is 2 or more, the halogen atoms may be the same or different. Each halogen atom may substitute at any position.

Examples of the alkyls or alkyl moieties in general formula (I) may include linear or branched $C_1$-$C_6$ groups such as methyl, ethyl, normal propyl, isopropyl, normal butyl, isobutyl, secondary butyl, tertiary butyl, normal pentyl, isopentyl, neopentyl, normal hexyl, and neohexyl.

In this description, there are cases where "tertiary" is expressed by "tert-".

Examples of the alkenyls or alkenyl moieties in general formula (I) may include linear or branched $C_2$-$C_6$ groups such as vinyl, 1-propenyl, 2-propenyl, isopropenyl, 2-methyl-1-propenyl, 1-methyl-1-propenyl, 2-methyl-2-propenyl, 1-methyl-2-propenyl, 1-butenyl, 2-butenyl, 3-butenyl, 1-pentenyl, 2-pentenyl, 2-methyl-2-butenyl, 1-hexenyl, and 2,3-dimethyl-2-butenyl.

Examples of the alkynyls or alkynyl moieties in general formula (I) may include linear or branched $C_2$-$C_6$ groups such as ethynyl, 1-propynyl, 2-propynyl, 1-butynyl, 2-butynyl, 3-butynyl, 1-methyl-2-propynyl, 2-methyl-3-butynyl, 3,3-dimethyl-1-butynyl, 1-hexynyl, 2-hexynyl, 3-hexynyl, 4-hexynyl, and 5-hexynyl.

Examples of the cycloalkyls or cycloalkyl moieties in general formula (I) may include $C_3$-$C_6$ groups such as cyclopropyl, cyclobutyl, cyclopentyl, and cyclohexyl.

The salt of the compound of general formula (I) may be any salts so long as the salts are acceptable to this technical field. Examples thereof may include: ammonium salts such as dimethylammonium salt and triethylammonium salt; inorganic acid salts, such as hydrochloride, perchlorate, sulfate, and nitrate; and organic acid salts, such as acetate, trifluoroacetate, oxalate, p-toluenesulfonate and methanesulfonate.

There are cases where a compound of general formula (I) or a salt thereof includes isomers such as optical isomers, both of the isomers and a mixture of the isomers are included in the present invention. In this description, isomers are given as a mixture thereof unless otherwise indicated. Incidentally, various isomers other than those shown above are included in the present invention so long as such isomers are within the range of common knowledge for this technical field. Although there are cases where some kinds of isomers have a chemical structure different from general formula (I), persons skilled in the art can sufficiently perceive such compounds to be isomers. It is therefore apparent that such isomers are within the scope of the present invention.

The compound of general formula (I) or salt thereof (hereinafter abbreviated to Invention Compound) can be produced in accordance with the following production processes and by ordinary processes for producing salts. However, usable methods for producing the Invention Compound are not limited to these processes.

Production Process [1]

The Invention Compound can be produced by reacting a compound of formula (II) with a compound of formula (III) in the presence of a palladium catalyst, a copper salt, and a base.

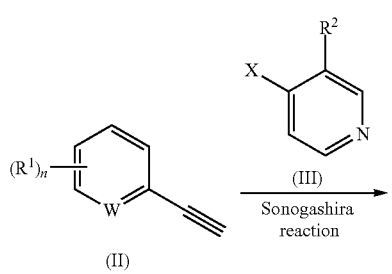

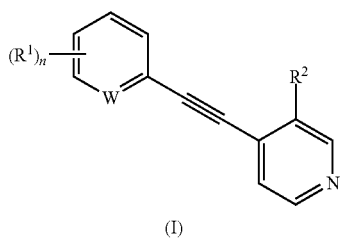

(In Production Process [1], X is a halogen atom, and n, $R^1$, $R^2$, and W are as defined above.)

Examples of the palladium catalyst may include tetrakis(triphenylphosphine)palladium(0) and bis(triphenylphosphine)palladium(II) dichloride.

Examples of the copper salt may include copper(I) iodide.

The base may be either an organic base or an inorganic base. Examples of the organic base may include amine bases such as triethylamine and diisopropylamine. Examples of the inorganic base may include alkali metal carbonates such as sodium carbonate, potassium carbonate, and cesium carbonate.

The reaction can be conducted in the presence of a solvent according to need. The solvent may be any solvent which is inert to the reaction. For example, one or more solvents can be suitably selected from: amine bases; aprotic polar solvents such as N,N-dimethylformamide and acetonitrile; ethers such as tetrahydrofuran; and the like.

With respect to reaction temperature, the reaction can be conducted at a temperature usually in the range of from about 20° C. to the boiling point of the solvent used. The reaction time can be usually from several minutes to 24 hours.

Production Process [2]

A compound of formula (I-b), which is general formula (I) in which $R^2$ is $NH_2$, can be produced by reducing a compound of formula (I-a), in which $R^2$ is $NO_2$, using a metal and an acid, or by a similar reaction.

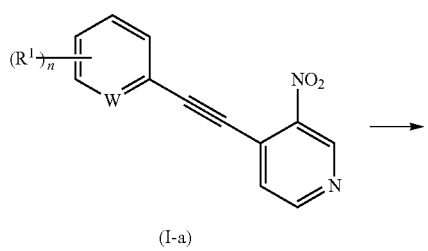

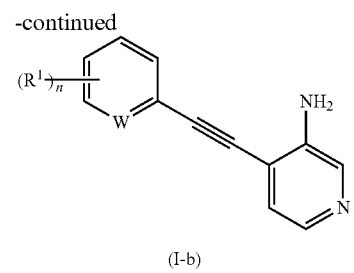

(In Production Process [2], n, $R^1$, and W are as defined above.)

Examples of the metal may include iron, zinc, and tin.

Examples of the acid may include inorganic acids such as hydrochloric acid and sulfuric acid and organic acids such as acetic acid.

The reaction can be conducted in the presence of a solvent according to need. The solvent may be any solvent which is inert to the reaction. For example, one or more solvents can be suitably selected from ethers such as tetrahydrofuran, ethylene glycol dimethyl ether, and 1,4-dioxane, esters such as methyl acetate and ethyl acetate, water, and the like, and mixed together and used.

With respect to reaction temperature, the reaction can be conducted at a temperature usually in the range of from about 20° C. to the boiling point of the solvent used. The reaction time can be usually from several minutes to 24 hours.

Production Process [3]

A compound of formula (I-c), which is general formula (I) in which $R^2$ is $NHR^3$, can be produced by reacting a compound of formula (I-b) with $R^3X$ in the presence of a base.

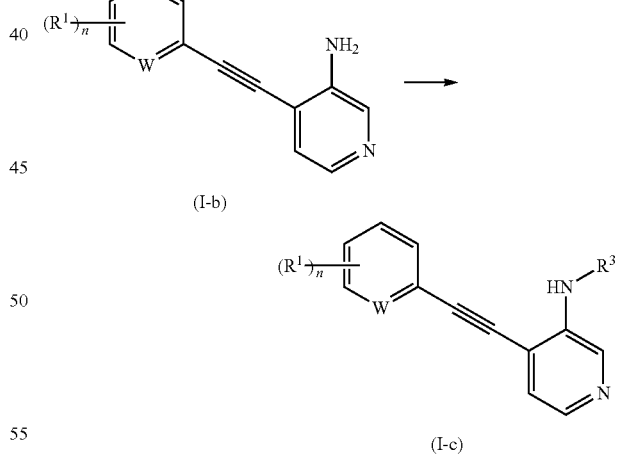

(In Production Process [3], $R^3$ represents a $(C_1-C_6)$alkyl group, a $(C_2-C_6)$alkenyl group, or a $(C_2-C_6)$alkynyl group. Symbols n, $R^1$, W, and X are as defined above.)

Examples of the base may include: alkali metal hydrides such as sodium hydride; alkali metal carbonates such as sodium carbonate, potassium carbonate, and cesium carbonate; and alkali metal hydroxides such as lithium hydroxide, sodium hydroxide, and potassium hydroxide.

The reaction can be conducted in the presence of a solvent according to need. The solvent may be any solvent which is inert to the reaction. For example, one or more solvents can be suitably selected from ethers such as tetrahydrofuran, ethylene glycol dimethyl ether, and 1,4-dioxane, acid amides such as N,N-dimethylformamide and N-methylpyrrolidinone, and the like, and mixed together and used.

With respect to reaction temperature, the reaction can be conducted at a temperature usually in the range of from about 20° C. to the boiling point of the solvent used. The reaction time can be usually from several minutes to 48 hours.

Production Process [4]

A compound of formula (I-d), which is general formula (I) in which $R^2$ is $NHCOR^4$, and a compound of formula (I-e), which is general formula (I) in which $R^2$ is $N(COR^4)_2$, can be produced by reacting a compound of formula (I-b) with a carboxylic acid halide $R^4COX$ or with a carboxylic acid anhydride $(R^4CO)_2O$.

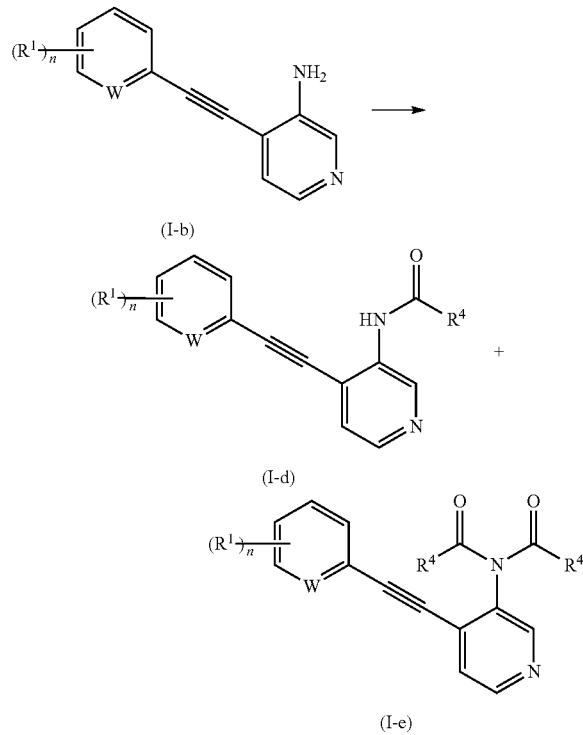

(In Production Process [4], $R^4$ represents a $(C_1$-$C_6)$alkyl group. Symbols n, $R^1$, W, and X are as defined above.)

The reaction can be conducted in the presence of a base according to need. Examples of the base may include: alkali metal hydrides such as sodium hydride; alkali metal carbonates such as potassium carbonate; alkali metal hydroxides such as sodium hydroxide; and amines such as triethylamine.

The reaction can be conducted in the presence of a solvent according to need. The solvent may be any solvent which is inert to the reaction. For example, one or more solvents can be suitably selected from ethers such as diethyl ether, tetrahydrofuran, ethylene glycol dimethyl ether, and 1,4-dioxane, acid amides such as N,N-dimethylformamide and N-methylpyrrolidinone, halogenated aliphatic hydrocarbons such as dichloromethane and chloroform, and the like, and mixed together and used.

With respect to reaction temperature, the reaction can be conducted at a temperature usually in the range of from about −20° C. to the boiling point of the solvent used. The reaction time can be usually from several minutes to 48 hours.

Production Process [5]

A compound of formula (I-f), which is general formula (I) in which $R^2$ is $SR^3$, can be produced by reacting a compound of formula (I-b) with an inorganic nitrite or with a nitrite ester to convert the compound of formula (I-b) into a diazonium compound and then reacting the diazonium compound with $R^3SH$ or $(R^3S)_2$.

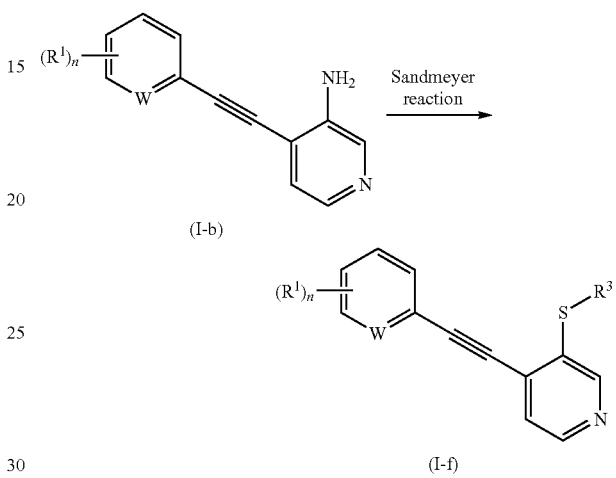

(In Production Process [5], n, $R^1$, $R^3$, and W are as defined above.)

Examples of the inorganic nitrite may include sodium nitrite and potassium nitrite.

Examples of the nitrite ester may include tert-butyl nitrite and isoamyl nitrite.

The reaction can be conducted in the presence of a copper catalyst according to need. Examples of the copper catalyst include copper(I) oxide and copper(II) sulfate pentahydrate.

The reaction can be conducted in the presence of an acid according to need. Examples of the acid may include: inorganic acids such as hydrochloric acid and sulfuric acid; and organic acids such as acetic acid and methanesulfonic acid.

The reaction can be conducted in the presence of a base according to need. Examples of the base include: alkali metal hydrides such as sodium hydride; alkali metal carbonates such as sodium carbonate, potassium carbonate, and cesium carbonate; and alkali metal hydroxides such as lithium hydroxide, sodium hydroxide, and potassium hydroxide.

The reaction can be conducted in the presence of a solvent according to need. The solvent can be one or more solvents suitably selected, for example, from: halogenated aliphatic hydrocarbons such as dichloromethane and chloroform; aromatic hydrocarbons such as toluene and xylene; aprotic polar solvents such as acetonitrile, N,N-dimethylformamide, and dimethyl sulfoxide; water; and the like.

With respect to reaction temperature, the reaction can be conducted at a temperature usually in the range of from −20° C. to 200° C. The reaction time can be usually from several minutes to 24 hours.

Production Process [6]

A compound of formula [I-g] can be produced by reacting a compound of formula (I-f) with an oxidizing agent.

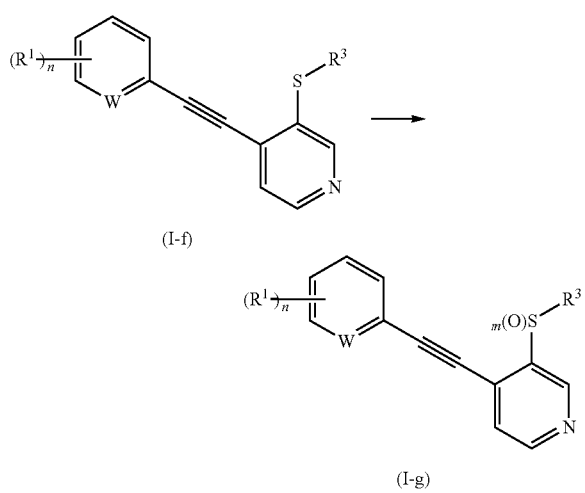

(I-f)

(I-g)

(In Production Process [6], m is 1 or 2, and n, $R^1$, $R^3$, and W are as defined above.)

Examples of the oxidizing agent may include: peroxides of carboxylic acids, such as 3-chloroperbenzoic acid; and hydrogen peroxide solutions.

Examples of solvents may include halogenated aliphatic hydrocarbons such as dichloromethane and chloroform.

With respect to reaction temperature, the reaction can be conducted at a temperature usually in the range of from about −20° C. to the boiling point of the solvent used. The reaction time can be usually from several minutes to 24 hours.

Production Process [7]

A compound of formula (I-h), which is general formula (I) in which $R^2$ is X, can be produced by converting a compound of formula (I-b) into a diazonium salt through reaction with an inorganic nitrite or a nitrite ester and then reacting the diazonium salt with a halogenating agent.

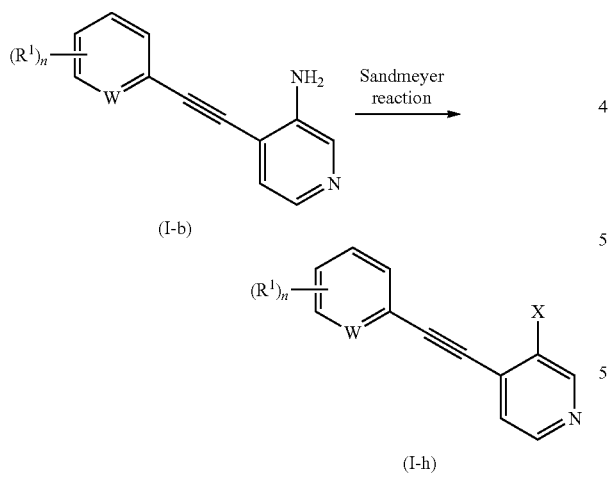

(I-b)

(I-h)

(In Production Process [7], n, $R^1$, W, and X are as defined above.)

Examples of the inorganic nitrite and examples of the nitrite ester may include the same salts and esters as those for Production Process [5].

Examples of the halogenating agent may include: halogens such as chlorine, bromine, and iodine; hydrohalogenic acids such as hydrochloric acid, hydrobromic acid, and hydroiodic acid; copper(I) halides such as copper(I) chloride, copper(I) bromide, and copper(I) iodide; copper(II) halides such as copper(II) chloride and copper(II) bromide; and tetrafluoroboric acid.

The reaction can be conducted in the presence of a copper catalyst according to need. Examples of the copper catalyst may include the copper(I) halides and copper(II) halides enumerated above, copper(I) oxide, and copper(II) sulfate pentahydrate.

The reaction can be conducted in the presence of an acid according to need. Examples of the acid may include: inorganic acids such as the hydrohalogenic acids enumerated above and sulfuric acid; and organic acids such as acetic acid and methanesulfonic acid.

The reaction can be conducted in the presence of a solvent according to need. Examples of the solvent may include the same solvents as those for Production Process [5], and one or more of these can be suitably selected, mixed together, and used.

With respect to reaction temperature, the reaction can be conducted at a temperature usually in the range of from −20° C. to 200° C. The reaction time can be usually from several minutes to 24 hours.

Production Process [8]

A compound of formula (I-c), which is general formula (I) in which $R^2$ is $NHR^3$, can be produced by the method shown by the following scheme.

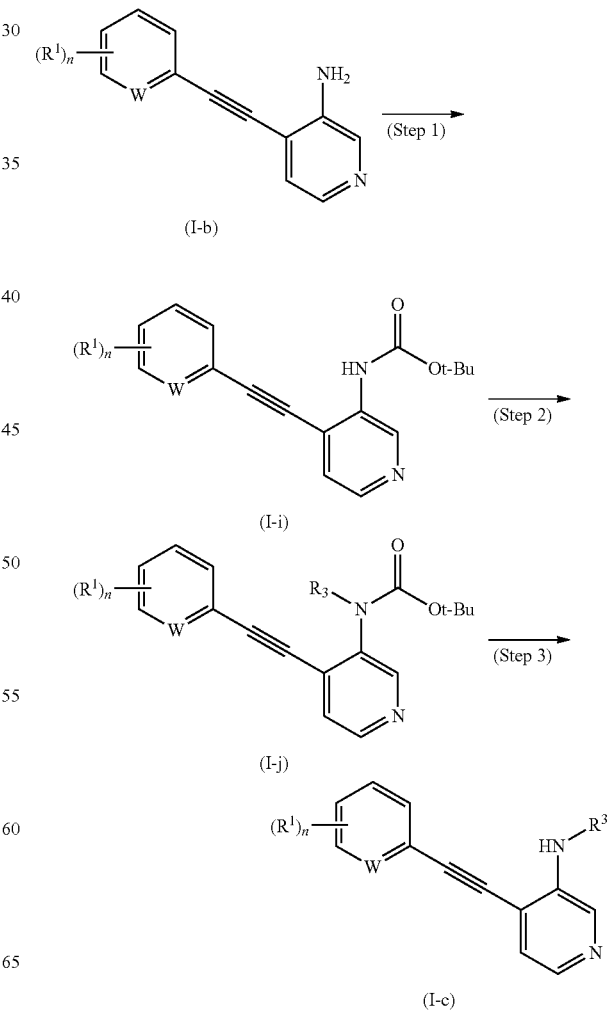

(I-b)

(I-i)

(I-j)

(I-c)

(In Production Process [8], t-Bu represents tertiary butyl. Symbols n, $R^1$, $R^3$, and W are as defined above.) (Step 1)

A compound of formula (I-i) can be produced by reacting a compound of formula (I-b) with di-tert-butyl dicarbonate in the presence of a base.

Examples of the base may include: alkali metal hydrides such as sodium hydride; alkali metal carbonates such as sodium carbonate, potassium carbonate, and cesium carbonate; alkali metal hydroxides such as lithium hydroxide, sodium hydroxide, and potassium hydroxide; and alkali metal amides such as lithium bis(trimethylsilyl)amide, sodium bis(trimethylsilyl)amide, and potassium bis(trimethylsilyl)amide.

The reaction can be conducted in the presence of a solvent according to need. The solvent may be any solvent which is inert to the reaction. Examples thereof may include the same solvents as those for Production Process [3], and one or more of these can be suitably selected, mixed together, and used.

With respect to reaction temperature, the reaction can be conducted at a temperature usually in the range of from about −20° C. to the boiling point of the solvent used. The reaction time can be usually from several minutes to 48 hours.

(Step 2)

A compound of formula (I-j) can be produced by reacting the compound of formula (I-i) with $R^3X$ (X is as defined above) in the presence of a base.

Examples of the base may include the same bases as those for Production Process [3].

The reaction can be conducted in the presence of a solvent according to need. Examples of the solvent may include the same solvents as those for Step 1, and one or more of these can be suitably selected, mixed together, and used.

With respect to reaction temperature, the reaction can be conducted at a temperature usually in the range of from about −20° C. to the boiling point of the solvent used. The reaction time can be usually from several minutes to 48 hours.

(Step 3)

The compound of formula (I-c) can be produced by reacting the compound (I-j) with an acid.

Examples of the acid may include inorganic acids such as hydrochloric acid and sulfuric acid and organic acids such as acetic acid.

The reaction can be conducted in the presence of a solvent according to need. The solvent can be any solvent which is inert to the reaction. Examples thereof may include the same solvents as those for Production Process [2], and one or more of these can be suitably selected, mixed together, and used.

With respect to reaction temperature, the reaction can be conducted at a temperature usually in the range of from about 0° C. to the boiling point of the solvent used. The reaction time can be usually from several minutes to 24 hours.

Intermediate Production Process [1]

The compound of formula (II) can be produced by the method shown by the following scheme.

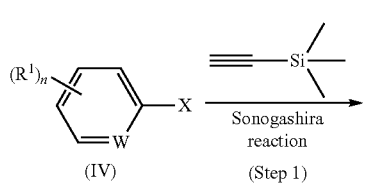

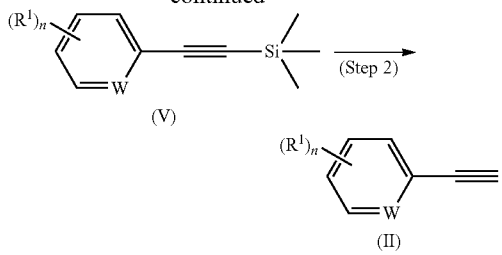

(In Intermediate Production Process [1], n, X, W, and $R^1$ are as defined above.)

(Step 1)

A compound of formula (V) can be produced by the Sonogashira reaction of a compound of formula (IV) with trimethylsilylacetylene (in accordance with Production Process [1]).

(Step 2)

The compound of formula (II) can be produced by reacting the compound of formula (V) with a base or tetrabutylammonium fluoride (TBAF).

Examples of the base may include: alkali metal carbonates such as potassium carbonate; and alkali metal hydroxides such as sodium hydroxide.

The reaction can be conducted in the presence of a solvent according to need. The solvent may be any solvent which is inert to the reaction. For example, one or more solvents can be selected from aprotic polar solvents such as acetone and acetonitrile, halogenated aliphatic hydrocarbons such as dichloromethane and 1,2-dichloroethane, esters such as ethyl acetate, ethers such as tetrahydrofuran and dioxane, protonic solvents such as methanol, and the like, and mixed together and used.

With respect to reaction temperature, the reaction can be conducted at a temperature usually in the range of from −90° C. to 50° C. The reaction time can be usually from several minutes to 24 hours.

Intermediate Production Process [2]

A compound of formula (III-a) can be produced by reacting a compound of formula (VI) with a base to yield a 4-halopyridine represented by formula (VII), subsequently reacting the 4-halopyridine with an alkyllithium or a lithium dialkylamide, and then reacting the resultant intermediate with $R^3X$.

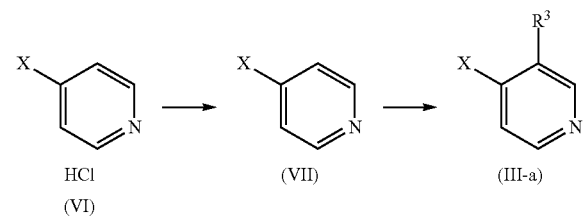

(In Intermediate Production Process [2], X and $R^3$ are as defined above.)

Examples of the base may include: alkali metal carbonates such as sodium carbonate, potassium carbonate, and cesium carbonate; and alkali metal hydroxides such as lithium hydroxide, sodium hydroxide, and potassium hydroxide.

Examples of the alkyllithium may include n-butyllithium, sec-butyllithium, and tert-butyllithium.

Examples of the lithium dialkylamide may include lithium diisopropylamide.

The reaction can be conducted in the presence of a solvent according to need. The solvent may be any solvent which is inert to the reaction. For example, one or more solvents can be suitably selected from ethers such as diethyl ether, tetrahydrofuran, ethylene glycol dimethyl ether, and 1,4-dioxane, aromatic hydrocarbons such as toluene and xylene, aliphatic hydrocarbons such as hexane, heptane, octane, and cyclohexane, and the like, and mixed together and used.

With respect to reaction temperature, the reaction can be conducted at a temperature usually in the range of from $-90°$ C. to $-50°$ C. The reaction time can be usually from several minutes to 24 hours.

Intermediate Production Process [3]

A compound of the formula (II-b), which is formula (II) in which $R^1$ is $OR^5$, can be produced by reacting a compound of formula (II-a) with $R^5X$ in the presence of a base.

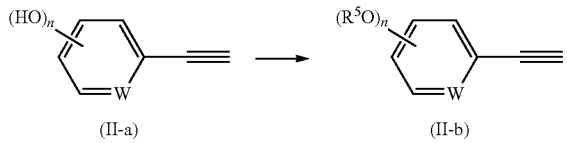

(In Intermediate Production Process [3], $R^5$ represents a $(C_1$-$C_6)$alkyl group, a $(C_r$ $C_6)$alkenyl group, a $(C_2$-$C_6)$alkynyl group, a $(C_1$-$C_6)$haloalkyl group, or a $(C_3$-$C_6)$cycloalkyl group. Symbols n, W, and X are as defined above.)

Examples of the base may include the same bases as those for Production Process [3].

The reaction can be conducted in the presence of a solvent according to need. The solvent may be any solvent which is inert to the reaction. Examples thereof may include the same solvents as those for Production Process [3], and one or more of these can be suitably selected, mixed together, and used.

With respect to reaction temperature, the reaction can be conducted at a temperature usually in the range of from about $20°$ C. to the boiling point of the solvent used. The reaction time can be usually from several minutes to 48 hours.

Intermediate Production Process [4]

A compound of formula (II-d), which is formula (II) in which $R^1$ is $SR^5$, can be produced by reacting a compound of formula (II-c) with $R^5X$ in the presence of a base.

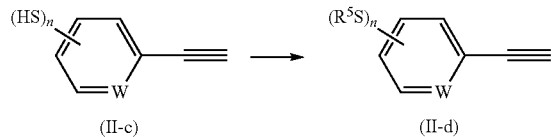

(In Intermediate Production Process [4], n, $R^5$, W, and X are as defined above.)

Examples of the base may include the same bases as those for Production Process [3].

The reaction can be conducted in the presence of a solvent according to need. The solvent may be any solvent which is inert to the reaction. Examples thereof may include the same solvents as those for Production Process [3], and one or more of these can be suitably selected, mixed together, and used.

With respect to reaction temperature, the reaction can be conducted at a temperature usually in the range of from about $20°$ C. to the boiling point of the solvent used. The reaction time can be usually from several minutes to 48 hours.

Intermediate Production Process [5] A compound of formula (II-f), which is formula (II) in which $R^1$ is $NHR^5$, can be produced by reacting a compound of formula (II-e) with $R^5X$ in the presence of a base.

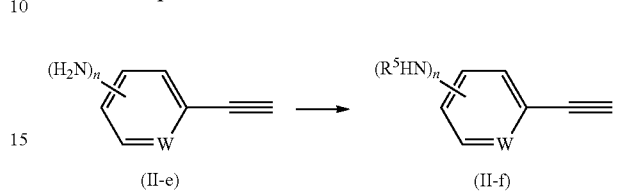

(In Intermediate Production Process [5], n, $R^5$, W, and X are as defined above.)

Examples of the base may include the same bases as those for Production Process [3].

The reaction can be conducted in the presence of a solvent according to need. The solvent may be any solvent which is inert to the reaction. Examples thereof may include the same solvents as those for Production Process [3], and one or more of these can be suitably selected, mixed together, and used.

With respect to reaction temperature, the reaction can be conducted at a temperature usually in the range of from about $20°$ C. to the boiling point of the solvent used. The reaction time can be usually from several minutes to 48 hours.

Intermediate Production Process [6]

A compound of formula (III-b), which is general formula (III) in which $R^2$ is $OR^3$, can be produced by the method shown by the following scheme from a compound of formula (VIII-a), which can be produced in accordance with the method described, for example, in WO 2005/101989. The compound of formula (III-b) can be taken out as an acid addition salt thereof by treating the compound with an acid.

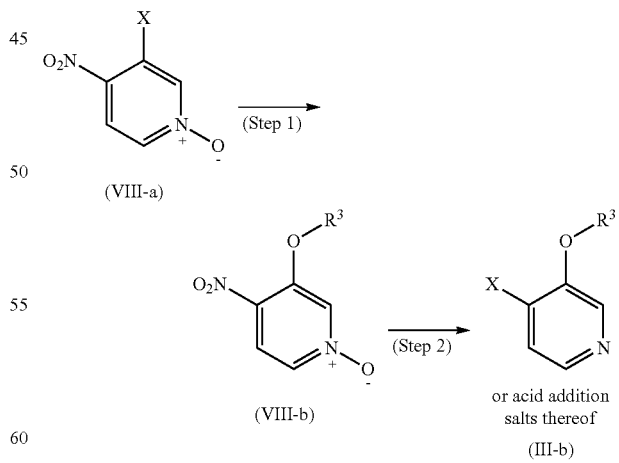

(In Intermediate Production Process [6], X and $R^3$ are as defined above.)

(Step 1)

A compound of formula (VIII-b) can be produced by reacting a compound of formula (VIII-a) with $R^3OM$ (M is Na, K, or Cs) or reacting a compound of formula (VIII-a) with R³OH in the presence of a base. Examples of the base may include the same bases as those for Production Process [3].

The reaction can be conducted in the presence of a solvent according to need. As the solvent, use can be made of one or more solvents suitably selected from alcohols such as methanol, ethanol, and 2-propanol, ethers such as diethyl ether, tetrahydrofuran, ethylene glycol dimethyl ether, and 1,4-dioxane, acid amides such as N,N-dimethylformamide and N-methylpyrrolidinone, and the like and mixed together.

With respect to reaction temperature, the reaction can be conducted at a temperature usually in the range of from about −20° C. to the boiling point of the solvent used. The reaction time can be usually from several minutes to 48 hours.

(Step 2)

The compound of formula (Ill-b) can be produced by subjecting the (VIII-b) to the action of a phosphorus trihalide. The desired compound can be produced also in the form of a salt by treating the obtained compound of formula (III-b) with an acid.

Examples of the phosphorus trihalide may include phosphorus trichloride and phosphorus tribromide.

The reaction can be conducted in the presence of a solvent according to need. As the solvent, use can be made of one or more solvents suitably selected from esters such as ethyl acetate, halogenated aliphatic hydrocarbons such as dichloromethane and chloroform, and the like and mixed together.

With respect to reaction temperature, the reaction can be conducted at a temperature usually in the range of from about −5° C. to the boiling point of the solvent used. The reaction time can be usually from several minutes to 48 hours.

Examples of the acid addition salt of the compound of formula (III-b) may include hydrochloride, sulfate, and acetate, and examples of the acid for the treatment may include hydrogen chloride, sulfuric acid, and acetic acid.

Intermediate Production Process [7]

A compound of formula (III-d), which is formula (I) in which R² is CH₂OR³, can be produced by reacting a compound of formula (III-c), which can be produced in accordance with the method described, for example, in Org. Lett., 2008, 10, 2701, with R³X in the presence of a base.

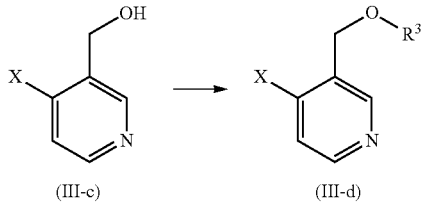

(III-c)    (III-d)

(In Intermediate Production Process [7], X and R³ are as defined above.)

Examples of the base may include the same bases as those for Production Process [3].

The reaction can be conducted in the presence of a solvent according to need. The solvent may be any solvent which is inert to the reaction. Examples thereof may include the same solvents as those for Production Process [3], and one or more of these can be suitably selected, mixed together, and used.

With respect to reaction temperature, the reaction can be conducted at a temperature usually in the range of from about −20° C. to the boiling point of the solvent used. The reaction time can be usually from several minutes to 48 hours.

Preferable embodiments of the pest control agent comprising the Invention Compound are described below. The pest control agent comprising the Invention Compound is useful, for example, as agents for controlling pests, mites, nematodes, or soil pests which are problematic in the agricultural and horticultural fields, namely, as agricultural or horticultural insecticides, miticides, nematicides, or soil pesticides. Furthermore, the pest control agent is useful as agents for controlling animal parasites, i.e., as agents for killing animal parasites.

The Invention Compound is useful as agricultural or horticultural insecticides, miticides, nematicides, or soil pesticides. The compound is specifically effective in controlling: pests including aphids such as green peach aphid and cotton aphid, agricultural pests such as diamondback moth, cutworm, common cutworm, codling moth, bollworm, tobacco budworm, gypsy moth, rice leafroller, smaller tea tortrix, colorado potato beetle, cucurbit leaf beetle, boll weevil, planthoppers, leafhoppers, scales, stinkbugs, whiteflies, thrips, grasshoppers, anthomyiids, scarabaeidae, black cutworm, turnip moth, and ants, gastropods such as slugs and snails, sanitary pests such as house tick, cockroaches, house fly, and common house mosquito, stored grain pests such as angoumois grain moth, azuki bean weevil, red flour beetle, and tenebrionids, and clothing or house pests such as clothes moth, black carpet beetle, and termites; mites including plant-parasitic mites such as two-spotted spider mite, carmine spider mite, kanzawa spider mite, citrus red mite, European red mite, broad mite, pink citrus rust mite, and bulb mite, and mites feeding on household dust, such as *Tyrophagus putrescentiae*, *Dermotophagoides farinae*, and *Chelacaropsis moorei*; nematodes including plant-parasitic nematodes such as root-knot nematodes, cyst nematodes, root-lesion nematodes, rice white-tip nematode, strawberry bud nematode, and pine wood nematode; and soil pests including isopods such as wood louse and pill bug. The agricultural or horticultural insecticide, miticide, nematicide, or soil pesticide which comprises the Invention Compound is especially effective in controlling plant-parasitic mites, agricultural pests, plant-parasitic nematodes, or the like, and is more highly effective in controlling plant-parasitic mites and agricultural pests, among those. Consequently, the agent according to the present invention is exceedingly useful as insecticides or miticides. Furthermore, the agricultural or horticultural insecticide, miticide, nematicide, or soil pesticide which comprises the Invention Compound is effective also in controlling various pests which are resistant to chemicals such as organophosphorus pesticides, carbamate pesticides, synthetic pyrethroid pesticides, neonicotinoid pesticides, or the like. Moreover, since the Invention Compound is excellent in terms of the property of infiltrating and migrating, not only soil insect pests, mites, nematodes, gastropods, isopods, or the like, but also pests living in or on the stalks and leaves can be controlled by treating the soil with the agricultural or horticultural insecticide, miticide, nematicide, or soil pesticide which comprises the Invention Compound.

Other preferable embodiments of the insecticide, miticide, nematicide, or soil pesticide which comprises the Invention Compound may include an agricultural or horticultural insecticide, miticide, nematicide, or soil pesticide for comprehensively controlling the plant-parasitic mites, agricultural pests, plant-parasitic nematodes, gastropods, soil pests, or the like, shown above.

Usually, the agricultural or horticultural insecticide, miticide, nematicide, or soil pesticide which comprises the Invention Compound is produced by mixing the compound with various agricultural additives to formulate the compound into various forms such as dusts, granules, water dispersible granules, wettable powders, water-based suspension concentrates, oil-based suspension concentrates, water-soluble granules, water-soluble powders, emulsifiable concentrates, soluble concentrates, pastes, aerosols, ultra low volume formulations, or the like, and is then used. The agent according to the present invention can be formulated into any preparations which are in common used in this field, so long as the preparation is suitable for the objects of the present invention. Examples of the additives for use in such preparations may include: solid carriers such as diatomaceous earth, slaked lime, calcium carbonate, talc, white carbon, kaolin, bentonite, kaolinite, sericite, clay, sodium carbonate, sodium bicarbonate, sodium sulfate, zeolite, and starch; solvents such as water, toluene, xylene, sorbent naphtha, dioxane, acetone, isophorone, methyl isobutyl ketone, chlorobenzene, cyclohexane, dimethyl sulfoxide, N,N-dimethylformamide, N,N-dimethylacetamide, N-methyl-2-pyrrolidone, and alcohols; anionic surfactants such as fatty acid salts, benzoate, alkylsulfosuccinate, dialkylsulfosuccinate, polycarboxylate, salts of alkylsulfuric acid ester, alkylsulfate, alkylarylsulfate, alkyl diglycol ether sulfate, salts of alcohol sulfuric acid ester, alkylsulfonate, alkylarylsulfonate, arylsulfonate, ligninsulfonate, (alkyldiphenyl ether)disulfonate, polystyrenesulfonate, salts of alkylphosphoric acid ester, alkylarylphosphate, styrylarylphosphate, salts of polyoxyethylene alkyl ether sulfuric acid ester, polyoxyethylene alkylaryl ether sulfate, salts of polyoxyethylene alkylaryl ether sulfuric acid ester, polyoxyethylene alkyl ether phosphate, salts of polyoxyethylene alkylaryl phosphoric acid ester, and salts of naphthalenesulfonic acid condensed with formaldehyde; nonionic surfactants such as sorbitan fatty acid esters, glycerin fatty acid esters, fatty acid polyglycerides, fatty acid alcohol polyglycol ethers, acetylene glycol, acetylene alcohol, oxyalkylene block polymers, polyoxyethylene alkyl ethers, polyoxyethylene alkylaryl ethers, polyoxyethylene styrylaryl ethers, poly(oxyethylene glycol)alkyl ethers, polyethylene glycol, polyoxyethylene fatty acid esters, polyoxyethylene sorbitan fatty acid esters, polyoxyethylene glycerin fatty acid esters, polyoxyethylene hydrogenated castor oil, and polyoxypropylene fatty acid esters; and vegetable oils and mineral oils, such as olive oil, kapok oil, castor oil, palm oil, *camellia* oil, coconut oil, sesame oil, corn oil, rice bran oil, peanut oil, cottonseed oil, soybean oil, rapeseed oil, linseed oil, tung oil, and liquid paraffins. One or more of these additive ingredients can be suitably selected and used, so long as the use thereof does not depart from the objects of the present invention. It is also possible to use additives suitably selected from additives which are known in this field other than the additives shown above. For example, use can be made of various additives in common use, such as fillers, thickeners, anti-settling agents, anti-freezing agents, dispersion stabilizers, safeners, and anti-mold agents. The mixing ratio (weight ratio) of the Invention Compound to such various additives may be from 0.001:99.999 to 95:5, preferably from 0.005:99.995 to 90:10. When those preparations are actually used, the preparations can be used as such or be used after the preparations are diluted to a given concentration with a diluent such as water, and various spreading agents (surfactants, vegetable oils, mineral oils, or the like) are added thereto according to need.

Methods for applying the agricultural or horticultural insecticide, miticide, nematicide, or soil pesticide which comprises the Invention Compound cannot be unconditionally specified because the methods depend on the weather conditions, type of preparation, time for application, application site, kind of the disease and pest, state of infestation thereof, or the like. However, the preparation formulated so as to have an active-ingredient concentration of generally 0.05-800,000 ppm, preferably 0.5-500,000 ppm, may be applied, and the amount of the preparation to be applied per unit area may be 0.05-50,000 g, preferably 1-30,000 g, in terms of the amount of the Invention Compound per hectare. Methods for controlling pests, mites, nematodes, or soil pests, in particular, for controlling plant-parasitic mites, agricultural pests, or plant-parasitic nematodes, by such application methods are included in the present invention.

Various preparations of the agricultural or horticultural insecticide, miticide, nematicide, or soil pesticide which comprises the Invention Compound or dilutions thereof can be usually applied by an application method in general use. Namely, the preparations or dilutions can be applied by aerial application (e.g., spraying, misting, atomizing, granule scattering, application to water surface, or the like), application to soil (mixing, irrigation, or the like), surface application (coating, dust coating, covering, or the like), use of an impregnated toxic bait, or the like. It is also possible to use a method in which the active ingredient is supplied as a mixture thereof with a feed to a farm animal to inhibit pests, in particular, insect pests, from breeding and growing on the excreta. Furthermore, the Invention Compound can be applied by the so-called ultra low volume application method. In this method, the active ingredient can be contained in a concentration of 100%.

The agricultural or horticultural insecticide, miticide, nematicide, or soil pesticide which comprises the Invention Compound can be used as a mixture or in combination with other agricultural chemicals, fertilizers, safeners, or the like, and there are cases where the agent according to the present invention shows an even better effect or function when used in such manner. Examples of the other agricultural chemicals may include herbicides, insecticides, miticides, nematicides, soil pesticides, bactericides, antiviral agents, attractants, antibiotics, plant hormones, and plant growth regulators. In particular, an insecticidal composition, miticidal composition, nematicidal composition, or soil-pesticidal composition in which the Invention Compound is used as a mixture or in combination with one or more active-ingredient compounds for other agricultural chemicals can attain preferable improvements in application range, time for chemical treatment, control activity, or the like. Incidentally, the Invention Compound and the active-ingredient compound(s) for other agricultural chemicals may be separately formulated and thereafter mixed together just before application thereof, or may be formulated together and used. Such insecticidal compositions, miticidal compositions, nematicidal compositions, or soil-pesticidal compositions are included in the present invention.

Examples of the active-ingredient compounds (common name, partly including names under application; or test codes according to Japan Plant Protection Association) for the insecticides, miticides, nematicides, or soil pesticides among the other agricultural chemicals include: organic phosphoric acid ester compounds such as profenofos, dichlorvos, fenamiphos, fenitrothion, EPN, diazinon, chlorpyrifos, chlorpyrifos-methyl, acephate, prothiofos, fosthiazate, cadusafos, dislufoton, isoxathion, isofenphos, ethion, etrimfos, quinalphos, dimethylvinphos, dimethoate, sulprofos, thiometon, vamidothion, pyraclofos, pyridaphenthion, pirimiphos-methyl, propaphos, phosalone, formothion, malathion, tetrachlorvinphos, chlorfenvinphos, cyanophos, trichlorfon, methidathion, phenthoate, ESP, azinphos-methyl, fenthion, heptenophos, methoxychlor, parathion, phosphocarb, demeton-S-methyl, monocrotophos, methamidophos, imicyafos, parathion-methyl, terbufos, phosphamidon, phosmet, phorate, phoxim and triazophos;

carbamate compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC and fenothiocarb;

nereistoxin derivatives such as cartap, thiocyclam, bensultap, thiosultap-sodium, thiosultap-disodium, monosultap, bisultap and thiocyclam hydrogen oxalate;

organic chlorine compounds such as dicofol, tetradifon, endosulfan, dienochlor and dieldrin;

organometallic compounds such as fenbutatin oxide and cyhexatin;

pyrethroid compounds such as fenvalerate, permethrin, cypermethrin, deltamethrin, cyhalothrin, tefluthrin, ethofenprox, flufenprox, cyfluthrin, fenpropathrin, flucythrinate, fluvalinate, cycloprothrin, lambda-cyhalothrin, pyrethrins, esfenvalerate, tetramethrin, resmethrin, protrifenbute, bifenthrin, zeta-cypermethrin, acrinathrin, alpha-cypermethrin, allethrin, gamma-cyhalothrin, theta-cypermethrin; tau-fluvalinate, tralomethrin, profluthrin, beta-cypermethrin, beta-cyfluthrin, metofluthrin, phenothrin, flumethrin and decamethrin;

benzoylurea compounds such as diflubenzuron, chlorfluazuron, teflubenzuron, flufenoxuron, triflumuron, hexaflumuron, lufenuron, novaluron, noviflumuron, bistrifluron and fluazuron;

juvenile hormone-like compounds such as methoprene, pyriproxyfen, fenoxycarb and diofenolan;

pyridazinone compounds such as pyridaben;

pyrazole compounds such as fenpyroximate, fipronil, tebufenpyrad, ethiprole, tolfenpyrad, acetoprole, pyrafluprole and pyriprole;

neonicotinoid compounds such as imidacloprid, nitenpyram, acetamiprid, thiacloprid, thiamethoxam, clothianidin, nidinotefuran, dinotefuran and nithiazine;

hydrazine compounds such as tebufenozide, methoxyfenozide, chromafenozide and halofenozide;

pyridine compounds such as pyridalyl and flonicamid;

cyclic keto-enol compounds such as spirodiclofen, spiromesifen and spirotetramat;

strobilurin compounds such as fluacrypyrim;

pyridinamine compounds such as flufenerim;

dinitro compounds;

organic sulfur compounds;

urea compounds;

triazine compounds;

hydrazone compounds; and other compounds including flometoquin, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, bifenazate, propargite, clofentezine, metaflumizone, flubendiamide, cyflumetofen, chlorantraniliprole, cyantraniliprole, cyclaniliprole, cyenopyrafen, pyrifluquinazon, fenazaquin, amidoflumet, sulfluramid, hydramethylnon, metaldehyde, HGW-86, ryanodine, verbutin, AKD-1022, chlorobenzoate, thiazolylcinnanonitrile, sulfoxaflor, fluensulfone, triflumezopyrim, afidopyropen, flupyradifuron, 3-bromo-N-(4-chloro-2-(1-cyclopropylethylcarbamoyl)-6-methylphenyl)-1-(3-chloropyridin-2-yl)-1H-pyrazole-5-carboxamide, 3-bromo-N-(2-bromo-4-chloro-6-(cyclopropylmethylcarbamoyl)phenyl)-1-(3-chloropyridin-2-yl)-1H-pyrazole-5-carboxamide, 3-bromo-N-(4-chloro-2-methyl-6-(methylcarbamoyl)phenyl)-1-(3-chloropyridin-2-yl)-1H-pyrazole-5-carboxamide, and 3-bromo-1-(3-chloropyridin-2-yl)-N-(4-cyano-2-methyl-6-(methylcarbamoyl)phenyl-1H-pyrazole-5-carboxamide.

Furthermore, the Invention Compound can be used as a mixture or in combination with: antibiotics and semisynthetic antibiotics, such as insecticidal crystal proteins produced by *Bacillus thuringiensis*, including *Bacillus thuringiensis aizawai*, *Bacillus thuringiensis kurstaki*, *Bacillus thuringiensis israelenisis*, *Bacillus thuringiensis japonensis*, and *Bacillus thuringiensis tenebrionis*, microbial pesticides such as entomopathogenic viral agents, entomopathogenic filamentous agents, and nematopathogenic filamentous agents, avermectin, emamectin Benzoate, milbemectin, milbemycin, spinosad, ivermectin, lepimectin, DE-175, abamectin, emamectin and spinetoram; natural substances such as azadirachtin and rotenone; repellents such as deet, or the like.

Examples of the active-ingredient compounds (common name, partly including names under application; or test codes according to Japan Plant Protection Association) for the bactericides among the other agricultural chemicals may include: anilinopyrimidine compounds such as mepanipyrim, pyrimethanil, cyprodinil and ferimzone;

triazolopyrimidine compounds such as 5-chloro-7-(4-methylpiperidin-1-yl)-6-(2,4,6-trifluorophenyl)[1,2,4]triazolo[1,5-a]pyrimidine;

pyridinamine compounds such as fluazinam;

azole compounds such as triadimefon, bitertanol, triflumizole, etaconazole, propiconazole, penconazole, flusilazole, myclobutanil, cyproconazole, tebuconazole, hexaconazole, furconazole-cis, prochloraz, metconazole, epoxiconazole, tetraconazole, oxpoconazole fumarate, sipconazole, prothioconazole, triadimenol, flutriafol, difenoconazole, fluquinconazole, fenbuconazole, bromuconazole, diniconazole, tricyclazole, probenazole, simeconazole, pefurazoate, ipconazole and imibenconazole;

quinoxaline compounds such as quinomethionate;

dithiocarbamate compounds such as maneb, zineb, mancozeb, polycarbamate, metiram, propineb and thiram;

organic chlorine compounds such as fthalide, chlorothalonil and quintozene;

imidazole compounds such as benomyl, cyazofamid, thiophanate-methyl, carbendazim, thiabendazole and fuberiazole;

cyanoacetamide compounds such as cymoxanil;

anilide compounds such as metalaxyl, metalaxyl-M, mefenoxam, oxadixyl, ofurace, benalaxyl, benalaxyl-M (kiralaxyl, chiralaxyl), furalaxyl, cyprofuram, carboxin, oxycarboxin, thifluzamide, boscalid, bixafen, isothianil, tiadinil and sedaxane;

sulfamide compounds such as dichlofluanid;

copper compounds such as cupric hydroxide and oxine copper;

isoxazole compounds such as hymexazol;

organophosphorus compounds such as fosetyl-Al, tolclofos-Methyl, S-benzyl O,O-diisopropyl phosphorothioate, O-ethyl S,S-diphenyl phosphorodithioate, aluminum ethyl hydrogen phosphonate, edifenphos and iprobenfos;

phthalimide compounds such as captan, captafol and folpet;

dicarboximide compounds such as procymidone, iprodione and vinclozolin;

benzanilide compounds such as flutolanil and mepronil;

amide compounds such as penthiopyrad, a mixture of 3-(difluoromethyl)-1-methyl-N-[(1RS,4SR,9RS)-1,2,3,4-tetrahydro-9-isopropyl-1,4-methanonaphthalen-5-yl]pyrazole-4-carboxamide and 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide (isopyrazam), silthiopham, fenoxanil and furametpyr;

benzamide compounds such as fluopyram and zoxamide;

piperazine compounds such as triforine;

pyridine compounds such as pyrifenox;

carbinol compounds such as fenarimol;

piperidine compounds such as fenpropidin;

morpholine compounds such as fenpropimorph and tridemorph;

organotin compounds such as fentin hydroxide and fentin acetate;

urea compounds such as pencycuron;

cinnamic acid compounds such as dimethomorph and flumorph;

phenyl carbamate compounds such as diethofencarb;

cyanopyrrole compounds such as fludioxonil and fenpiclonil;

strobilurin compounds such as azoxystrobin, kresoxim-methyl, metominostrobin, trifloxystrobin, picoxystrobin, oryzastrobin, dimoxystrobin, pyraclostrobin and fluoxastrobin;

oxazolidinone compounds such as famoxadone;

thiazolecarboxamide compounds such as ethaboxam;

valine amide compounds such as iprovalicarb and benthiavalicarb-isopropyl;

acylamino acid compounds such as methyl N-(isopropoxycarbonyl)-L-valyl-(3RS)-3-(4-chlorophenyl)-β-alaninate (valiphenalate);

imidazolinone compounds such as fenamidone;

hydroxyanilide compounds such as fenhexamid;

benzenesulfonamide compounds such as flusulfamide;

oxime ether compounds such as cyflufenamid;

anthraquinone compounds;

crotonic acid compounds;

antibiotics such as validamycin, kasugamycin and polyoxins;

guanidine compounds such as iminoctadine and dodine;

quinoline compounds such as 6-tert-butyl-8-fluoro-2,3-dimethylquinolin-4-yl acetate (tebufloquin);

thiazolidine compounds such as (Z)-2-(2-fluoro-5-(trifluoromethyl)phenylthio)-2-(3-(2-methoxyphenyl)thiazolidin-2-yldene)acetonitrile (flutianil); and other compounds including pyribencarb, isoprothiolane, pyroquilon, diclomezine, quinoxyfen, propamocarb hydrochloride, chloropicrin, dazomet, metam-sodium, nicobifen, metrafenone, UBF-307, diclocymet, proquinazid, amisulbrom (amibromdole), 3-(2,3,4-trimethoxy-6-methylbenzoyl)-5-chloro-2-methoxy-4-methylpyridine, 4-(2,3,4-trimethoxy-6-methylbenzoyl)-2,5-dichloro-3-trifluoromethylpyridine, pyriofenone, isofetamid, mandipropamid, fluopicolide, carpropamid, meptyldinocap, N-[(3',4'-dichloro-1,1-dimethyl)phenacyl]-3-trifluoromethyl-2-pyridinecarboxamide, N-[(3',4'-dichloro-1,1-dimethyl)phenacyl]-3-methyl-2-thiophenecarboxamide, N-[(3',4'-dichloro-1,1-dimethyl)phenacyl]-1-methyl-3-trifluoromethyl-4-pyrazolecarboxamide, N-[[2'-methyl-4'-(2-propyloxy)-1,1-dimethyl]phenacyl]-3-trifluoromethyl-2-pyridinecarboxamide, N-[[2'-methyl-4'-(2-propyloxy)-1,1-dimethyl]phenacyl]-3-methyl-2-thiophenecarboxamide, N-[[2'-methyl-4'-(2-propyloxy)-1,1-dimethyl]phenacyl]-1-methyl-3-trifluoromethyl-4-pyrazolecarboxamide, N-[[4'-(2-propyloxy)-1,1-dimethyl]phenacyl]-3-trifluoromethyl-2-pyridinecarboxamide, N-[[4'-(2-propyloxy)-1,1-dimethyl]phenacyl]-3-methyl-2-thiophenecarboxamide, N-[[4'-(2-propyloxy)-1,1-dimethyl]phenacyl]-1-methyl-3-trifluoromethyl-4-pyrazolecarboxamide, N-[[2'-methyl-4'-(2-pentyloxy)-1,1-dimethyl]phenacyl]-3-trifluoromethyl-2-pyridinecarboxamide, N-[[4'-(2-pentyloxy)-1,1-dimethyl]phenacyl]-3-trifluoromethyl-2-pyridinecarboxamide, spiroxamine, S-2188 (fenpyrazamine), S-2200, ZF-9646, BCF-051, BCM-061, and BCM-062.

Other examples of agricultural chemicals which can be used as a mixture or in combination with the Invention Compound may include active-ingredient compounds for herbicides, in particular, herbicides of the soil application type, such as those given in The Pesticide Manual (15th edition).

In the case where the Invention Compound is used as an agent for killing animal parasites, this agent is effective specifically in controlling noxious ectoparasites which are parasitic on the body surface (the back, axillae, abdomen, inside of thigh, or the like) of host animals and noxious endoparasites which are parasitic in the inside (the stomach, intestinal tract, lungs, heart, liver, blood vessels, subcutaneous tissues, lymphatic tissues, or the like) of host animals. In particular, the agent is effective in controlling ectoparasites.

Examples of the ectoparasites may include animal-parasitic mites and fleas. Since the number of kinds of these parasites is exceedingly large and it is difficult to enumerate all, examples thereof are shown below.

Examples of the animal-parasitic mites may include: ticks such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus*, and *Dermacentor taiwanesis; Dermanyssus gallinae*; northern fowl mites such as *Ornithonyssus sylviarum* and *Ornithonyssus bursa*; trombiculids such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi*, and *Helenicula miyagawai*; cheyletids such as *Cheyletiella yasguri, Cheyletiella parasitivorax*, and *Cheyletiella blakei*; sarcoptids such as *Psoroptes cuniculi, Chorioptes bovis, Otodectes cynotis, Sarcoptes scabiei*, and *Notoedres cati*; and demodexes such as *Demodex canis*. The agent for killing animal parasites, which comprises the Invention Compound, is especially effective in controlling ticks among those.

Examples of the animal-parasitic fleas may include ectoparasitic wingless insects belonging to the order Siphonaptera. More specific examples thereof may include fleas belonging to the families Pulicidae, Ceratephyllus, and the like. Examples of the fleas belonging to the family Pulicidae may include *Ctenocephalides canis Ctenocephalides felis, Pulex irritans Echidnophaga gallinacea, Xenopsylla cheopis, Leptopsylla semis, Nosopsyllus fasciatus*, and *Monopsyllus anisus*. The agent for killing animal parasites, which comprises the Invention Compound, is especially effective in controlling fleas belonging to the family Pulicidae among those, in particular, *Ctenocephalides canis, Ctenocephalides felis*, and the like.

Examples of other ectoparasites may include: lice such as cattle louse, horse louse, sheep louse, longnosed cattle louse, and head louse; chewing lice such as dog chewing louse; and blood-sucking dipterous pests such as horseflies, biting midges, and black flies. Examples of the endoparasites may include: nematodes such as lungworms, whipworms, tuberous worms, gastric parasites, roundworms, and filariae; cestodes such as *Spirometra erinaceieuropaei, Diphyllobothrium latum, Dipylidium caninum, Taenia multiceps, Echinococcus granulosus,* and *Echinococcus multilocularis*; trematodes such as *Schistosoma japonicum* and fasciolae; and protozoans such as coccidia, malaria parasites, intestinal sarcocystises, toxoplasmas, and cryptosporidia.

Examples of the host animals may include various pet animals, farm animals, and poultry. More specific examples thereof may include dogs, cats, mice, rats, hamsters, guinea pigs, squirrels, rabbits, ferrets, birds (e.g., pigeons, parrots, hill mynas, Java sparrows, parakeets, society finches, canaries, or the like), cattle, horses, pigs, sheep, ducks, and chickens. The agent for killing animal parasites, which comprises the Invention Compound, is effective in controlling pests or mites which are ectoparasitic on pet animals or farm animals, among those. The agent is especially effective for dogs, cats, cattle, or horses among the pet animals and farm animals.

In the case where the Invention Compound is used as an agent for killing animal parasites, the compound may be used as such or can be used after having been formulated together with adequate additives into various forms such as dusts, granules, tablets, powders, capsules, liquid formulations, emulsifiable concentrates, water-based suspensions, oil-based suspensions, or the like. Besides being formulated into such forms, the Invention Compound can be formulated into any preparations which are in common use in this field, so long as the preparation is suitable for the objects of the present invention. Examples of the additives for use in the preparations may include: the anionic surfactants and nonionic surfactants shown above as examples of the additives for formulating the agricultural or horticultural insecticide, miticide, nematicide, or soil pesticide; cationic surfactants such as cetyltrimethylammonium bromide; solvents such as water, acetone, acetonitrile, N-methylacetamide, N,N-dimethylacetamide, N,N-dimethylformamide, 2-pyrrolidone, N-methyl-2-pyrrolidone, kerosene, triacetin, methanol, ethanol, isopropanol, benzyl alcohol, ethylene glycol, propylene glycol, polyethylene glycol, liquid polyoxyethylene glycol, butyl diglycol, ethylene glycol monomethyl ether, ethylene glycol monoethyl ether, diethylene glycol monoethyl ether, diethylene glycol n-butyl ether, dipropylene glycol monomethyl ether, and dipropylene glycol n-butyl ether; antioxidants such as butylhydroxyanisole, butylhydroxytoluene, ascorbic acid, sodium hydrogen metasulfite, propylgallate, and sodium thiosulfate; film-forming agents such as polyvinylpyrrolidone, polyvinyl alcohol, and copolymers of vinyl acetate and vinylpyrrolidone; the vegetable oils and mineral oils shown above as examples of the additives for formulating the agricultural or horticultural insecticide, miticide, nematicide, or soil pesticide; and carriers such as lactose, sucrose, glucose, starch, flour, corn flour, soybean oil cake, de-fatted rice bran, calcium carbonate, and other commercial raw materials for feeds. One or more of these additive ingredients can be suitably selected and used, so long as the use thereof does not depart from the objects of the present invention. It is also possible to use additives suitably selected from additives which are known in this field other than the additives shown above. Furthermore, use can be made of one or more ingredients suitably selected from the various additives mentioned above for use in the agricultural and horticultural fields.

The mixing ratio (weight ratio) of the Invention Compound to such various additives is usually about from 0.1:99.9 to 90:10. When those preparations are actually used, the preparations can be used as such or be used after the preparations are diluted to a given concentration with a diluent such as water, and various spreading agents (surfactants, vegetable oils, mineral oils, or the like) are added thereto according to need.

The Invention Compound is administered to the host animal perorally or parenterally. Examples of methods for the peroral administration may include a method of administering a tablet, liquid formulation, capsule, wafer, biscuit, minced meat, another feed, or the like which comprises the Invention Compound. Examples of methods for the parenteral administration may include: a method in which the Invention Compound is formulated into an adequate preparation and this preparation is introduced into the body by administration by intravenous injection, intramuscular administration, intracutaneous administration, subcutaneous administration, or the like; a method in which the Invention Compound is administrated to the body surface by a spot-on treatment, pour-on treatment, spraying, or the like; and a method in which a resin piece or the like which comprises the Invention Compound is buried under the skin of the host animal.

The amount of the Invention Compound to be administrated to a host animal varies depending on the method of administration, purpose of the administration, condition of the disease, or the like. However, it is adequate to administer the compound in a dose of usually 0.01 mg to 100 g, preferably 0.1 mg to 10 g, per kg of the body weight of the host animal.

Methods for controlling animal parasites, in particular, for controlling ectoparasites or endoparasites, by the method or amount of administration as described above are included in the present invention.

In the present invention, there are cases where by thus controlling noxious animal parasites, the various diseases of the host animals which are attributable to the parasites can be prevented or remedied. Consequently, prophylactic or therapeutic agents for parasitic animal diseases, comprising the Invention Compound as an active ingredient, and methods for preventing or remedying parasitic animal diseases therewith are included in the present invention.

When the Invention Compound is used as an agent for killing animal parasites, the compound can be used as a mixture or in combination with various kinds of vitamins, minerals, amino acids, nutrients, preparations of ferments, antipyretic agents, sedative agents, anti-inflammatory agents, bactericides, colorants, fragrances, preservatives, or the like, together with additives. The Invention Compound can be used as a mixture or in combination with other various drugs for animals or various agricultural chemicals, such as, for example, anthelminthic agents, anticoccidial agents, insecticides, miticides, agents for killing fleas, nematicides, bactericides, antibacterial agents, or the like, according to need, and there are cases where the Invention Compound shows an even better effect when used in such manner. Compositions for controlling animal parasites, the compositions comprising the Invention Compound as a mixture or in combination with various ingredients such as those shown above, and methods for controlling animal parasites, in particular, for controlling ectoparasites or endoparasites, using the compositions are included in the present invention.

EXAMPLES

Examples of the present invention are given below, but the present invention should not be construed as being limited to the following Examples. First, Synthesis Examples of the Invention Compounds are given.

Synthesis Example 1

Synthesis of 4-((4-tert-butyl)phenyl)ethynyl)-3-nitropyridine (Compound No. 13)

In a nitrogen atmosphere, 4-chloro-3-nitropyridine (5.0 g, 31.6 mmol), 4-tert-butylphenylacetylene (5.0 g, 31.6 mmol), triethylamine (1.3 mL, 93.3 mmol), bis(triphenylphosphine) palladium(II) dichloride (1.1 g, 1.6 mmol), copper(I) iodide (0.3 g, 1.6 mmol), and N,N-dimethylformamide (60 mL) were stirred at room temperature for 15 hours. To the reaction solution were added water and ethyl acetate. Thereafter, the mixture solution was filtered with a Celite and extracted with ethyl acetate. The organic layer was washed with brine and dried with anhydrous sodium sulfate. After anhydrous sodium sulfate was removed by filtration, the solvent was distilled off under reduced pressure and the residue was purified by silica gel column chromatography (eluent: n-heptane/ethyl acetate=from 95/5 to 80/20 by volume) to obtain the desired substance (7.6 g; yield, 85%).

Synthesis Example 2

Synthesis of 3-allyl-4-((4-tert-butylphenyl)ethynyl) pyridine (Compound No. 17)

(1) Synthesis of 3-allyl-4-bromopyridine

Toluene (25 mL) and 3M aqueous sodium hydroxide solution (15 mL) were added to 4-bromopyridine hydrochloride (5.0 g, 25.7 mmol) with cooling with ice, followed by stirring for 30 minutes with ice cooling. The reaction mixture was separated, and anhydrous sodium sulfate was added to the organic layer to dry the layer. Thereafter, the anhydrous sodium sulfate was removed by filtration. Tetrahydrofuran (50 mL) was added to the toluene solution of 4-bromopyridine thus obtained. In a nitrogen atmosphere, the resultant mixture was cooled to −78° C., and a 1M hexane/tetrahydrofuran solution of lithium diisopropylamide (25 mL) was added dropwise thereto, followed by stirring at that temperature for 1 hour. Allyl iodide (2.5 mL, 27.4 mmol) was added dropwise thereto at −78° C., and this mixture was heated to room temperature over 3 hours. Brine was added to the reaction mixture, and the resultant mixture was separated. Anhydrous sodium sulfate was added to the organic layer to dry the layer. After anhydrous sodium sulfate was removed by filtration, the solvent was distilled off under reduced pressure and the residue was purified by silica gel column chromatography (eluent: n-heptane/ethyl acetate=90/10 by volume) to obtain 3-allyl-4-bromopyridine (0.95 g; yield, 19%).

(2) Synthesis of the Desired Substance 3-allyl-4-bromopyridine (500 mg, 2.5 mmol), 4-tert-butylphenylacetylene (400 mg, 2.5 mmol), copper(I) iodide (30 mg, 0.16 mmol), bis(triphenylphosphine)palladium(II) dichloride (90 mg, 0.13 mmol), triethylamine (1 mL, 7.2 mmol), and N,N-dimethylformamide (5 mL) were reacted at 90° C. for 5 hours in a nitrogen atmosphere. After the reaction solution was allowed to cool to room temperature, water was added thereto, followed by extracting with ethyl acetate. The organic layer was washed with water and brine, and then anhydrous sodium sulfate was added to the washed organic layer to dry the layer. After anhydrous sodium sulfate was removed by filtration, the solvent was distilled off under reduced pressure and the residue was purified by silica gel column chromatography (eluent: n-heptane/ethyl acetate=90/10 by volume) to obtain the desired substance (500 mg; yield, 72%).

Synthesis Example 3

Synthesis of 4-((4-(tert-butyl)phenyl)ethynyl)pyridine-3-amine (Compound No. 30)

4-((4-(tert-butyl)phenyl)ethynyl)-3-nitropyridine (7.6 g, 27.0 mmol) and iron (4.5 g, 81.0 mmol) were added to a mixture solution of ethyl acetate (30 mL), acetic acid (15 mL), and water (15 mL). This mixture was reacted for 1 hour with refluxing. After the reaction solution was filtered with a Celite, the solvent was distilled off under reduced pressure and the residue was extracted with ethyl acetate. The organic layer was washed with saturated aqueous sodium hydrogen carbonate solution and brine and dried with anhydrous sodium sulfate. After anhydrous sodium sulfate was removed by filtration, the solvent was distilled off under reduced pressure and the residue was purified by silica gel column chromatography (eluent: n-heptane/ethyl acetate=30/70 by volume) to obtain the desired substance (7.2 g; yield, 100%).

Synthesis Example 4

Synthesis of 4-((4-(tert-butyl)phenyl)ethynyl)-3-(methylthio)pyridine (Compound No. 26)

In chloroform (3 mL) were dissolved 4-((4-(tert-butyl)phenyl)ethynyl)pyridine-3-amine (400 mg, 1.6 mmol) and dimethyl disulfide (301 mg, 3.2 mmol), followed by cooling with ice. To the solution was dropwise added a solution of tert-butyl nitrite (214 mg, 2.1 mmol) in chloroform (2 mL). Thereafter, this mixture was stirred for 10 minutes with cooling with ice, subsequently heated to 80° C., and then stirred for 1 hour. After the reaction mixture was allowed to cool to room temperature, the solvent was distilled off under reduced pressure and the residue was purified by flash chromatography to obtain the desired substance (184 mg; yield, 41%).

Synthesis Example 5

Synthesis of 4-((4-(tert-butyl)phenyl)ethynyl)-N-propylpyridine-3-amine (Compound No. 32)

In N,N-dimethylformamide (5 mL) was dissolved 4-((4-(tert-butyl)phenyl)ethynyl)pyridine-3-amine (300 mg, 1.2 mmol), followed by cooling with ice. 60% Sodium hydride (60 mg, 1.5 mmol) was added to the solution, and this mixture was stirred for 20 minutes with cooling with ice. Thereafter, 1-iodopropane (300 mg, 1.8 mmol) was added thereto, and the resultant mixture was stirred at 80° C. for 5 hours. After the reaction solution was allowed to cool to room temperature, water was added thereto, followed by extracting with ethyl acetate. The organic layer was washed with brine and dried with anhydrous sodium sulfate. After anhydrous sodium sulfate was removed by filtration, the solvent was distilled off under reduced pressure and the residue was purified by silica gel column chromatography (eluent: n-heptane/ethyl acetate=70/30 by volume) to obtain the desired substance (45 mg; yield, 13%).

Synthesis Example 6

Synthesis of 4-((4-(tert-butyl)phenyl)ethynyl)-3-(methylsulfinyl)pyridine (Compound No. 37) and 4-((4-(tert-butyl)phenyl)ethynyl)-3-(methylsulfonyl) pyridine (Compound No. 41)

In chloroform (2 mL) was dissolved 4-((4-(tert-butyl) phenyl)ethynyl)-3-(methylthio)pyridine (83 mg, 0.3 mmol), followed by cooling with ice. Thereto was added 3-chloroperbenzoic acid (100 mg, 0.6 mmol) and this mixture was stirred for 2 hours with cooling with ice. Water was added to the resultant reaction solution, followed by extracting with ethyl acetate. The organic layer was dried with anhydrous sodium sulfate. After anhydrous sodium sulfate was removed by filtration, the solvent was distilled off under reduced pressure and the residue was purified by flash chromatography to obtain Compound No. 37 (26 mg; yield, 30%) and Compound No. 41 (31 mg; yield, 33%).

Synthesis Example 7

Synthesis of N-(4-((4-(tert-butyl)phenyl)ethynyl) pyridin-3-yl)propionamide (Compound No. 59) and N-(4-((4-(tert-butyl)phenyl)ethynyl)pyridin-3-yl)-N-propionylpropionamide (Compound No. 60)

In N,N-dimethylformamide (10 mL) were dissolved 4-((4-(tert-butyl)phenyl)ethynyl)pyridine-3-amine (300 mg, 1.2 mmol) and triethylamine (1.0 mL, 7.2 mmol), followed by cooling with ice. Propionyl chloride (550 mg, 6.0 mmol) was added dropwise to the solution, and the resultant mixture was thereafter stirred at room temperature for 16 hours. Water was added to the reaction solution, followed by extracting with ethyl acetate. The organic layer was washed with brine and dried with anhydrous sodium sulfate. After anhydrous sodium sulfate was removed by filtration, the solvent was distilled off under reduced pressure and the residue was purified by silica gel column chromatography (eluent: n-heptane/ethyl acetate=from 80/20 to 60/40 by volume) to obtain Compound No. 59 (73 mg; yield, 20%) and Compound No. 60 (91 mg; yield, 20%).

Synthesis Example 8

Synthesis of 1-(4-((3-allylpyridin-4-yl)ethynyl)phenyl)ethanone (Compound No. 92)

(1) Synthesis of 1-(4-(((trimethylsilyl)ethynyl)phenyl)ethanone

In a nitrogen atmosphere, 4-iodoacetophenone (1.2 g, 4.9 mmol), trimethylsilylacetylene (1.0 g, 10 mmol), copper(I) iodide (50 mg, 0.26 mmol), bis(triphenylphosphine)palladium(II) dichloride (170 mg, 0.24 mmol), triethylamine (2.0 mL, 14 mmol), and N,N-dimethylformamide (10 mL) were reacted at 80° C. for 16 hours. After this reaction solution was allowed to cool to room temperature, water was added thereto, followed by extracting with ethyl acetate. The organic layer was washed with water and brine, and anhydrous sodium sulfate was added to dry the layer. After anhydrous sodium sulfate was removed by filtration, the solvent was distilled off under reduced pressure and the residue was purified by flash chromatography to obtain 1-(4-(((trimethylsilyl)ethynyl)phenyl)ethanone (0.91 g; yield, 84%).

(2) Synthesis of 1-(4-ethynylphenyl)ethanone 1-(4-(((trimethylsilyl)ethynyl)phenyl)ethanone (0.86 g, 4.0 mmol), potassium carbonate (1.1 g, 8.0 mmol), and methanol (8 mL) were reacted at room temperature for 1 hour. After the solvent was distilled off under reduced pressure, water was added thereto, followed by extracting with ethyl acetate. The organic layer was washed with water and brine, and anhydrous sodium sulfate was added to dry the layer. After anhydrous sodium sulfate was removed by filtration, the solvent was distilled off under reduced pressure and the residue was purified by flash chromatography to obtain 1-(4-ethynylphenyl)ethanone (0.53 g; yield, 91%).

(3) Synthesis of the Desired Substance

In a nitrogen atmosphere, 3-allyl-4-bromopyridine (200 mg, 1 mmol), 1-(4-ethynylphenyl)ethanone (160 mg, 1.1 mmol), copper(I) iodide (10 mg, 0.05 mmol), tetrakis(triphenylphosphine)palladium(0) (60 mg, 0.05 mmol), triethylamine (4 mL), and N,N-dimethylformamide (4 mL) were reacted at 50° C. for 24 hours. After the reaction mixture was allowed to cool to room temperature, water was added thereto, followed by extracting with ethyl acetate. The organic layer was washed with water and brine, and anhydrous sodium sulfate was added to dry the layer. After anhydrous sodium sulfate was removed by filtration, the solvent was distilled off under reduced pressure and the residue was purified by flash chromatography to obtain the desired substance (90 mg; yield, 34%).

Synthesis Example 9

Synthesis of 3-bromo-4-((4-(tert-butyl)phenyl)ethynyl)pyridine (Compound No. 10)

A mixture solution of tert-butyl nitrite (0.61 g, 5.92 mmol) and acetonitrile (5 mL) was added dropwise to a mixture solution of 4-((4-(tert-butyl)phenyl)ethynyl)pyridine-3-amine (1.0 g, 3.99 mmol) and acetonitrile (25 mL), with cooling with ice. After the dropwise addition, the mixture was stirred at that temperature for 30 minutes. Copper(II) bromide (1.12 g, 5.01 mmol) was added thereto. Thereafter, the resultant mixture was heated to room temperature and stirred for 15 hours at the temperature. Ethyl acetate (50 mL) and water (50 mL) were added to the reaction mixture, and the undissolved matter was removed by filtration with a Celite. This reaction mixture was extracted with ethyl acetate, and the organic layer was washed with brine, and anhydrous sodium sulfate was added to dry the layer. After anhydrous sodium sulfate was removed by filtration, the solvent was distilled off under reduced pressure. The residue was purified by flash chromatography to obtain the desired substance (0.36 g; yield, 29%).

Synthesis Example 10

Synthesis of 4-((4-(tert-butyl)phenyl)ethynyl)-3-methoxypyridine (Compound No. 21)

(1) Synthesis of 3-methoxy-4-nitropyridine 1-oxide

To a mixture suspension of 3-fluoro-4-nitropyridine 1-oxide (9.75 g, 61.7 mmol) and methanol (145 mL) was added 28% sodium methoxide methanol solution (11.9 g, 61.7 mmol) with cooling with ice. This mixture was heated to room temperature and stirred for 1 hour at the temperature. The methanol was distilled off under reduced pressure. Water (50 mL) was added to the residue, followed by extracting with chloroform. The organic layer was washed with brine, and anhydrous sodium sulfate was added to dry the layer. After anhydrous sodium sulfate was removed by filtration, the solvent was distilled off under reduced pressure to obtain 3-methoxy-4-nitropyridine 1-oxide (9.54 g; yield, 91%).

(2) Synthesis of 4-bromo-3-methoxypyridine hydrochloride

At room temperature, phosphorus tribromide (45 mL, 477 mmol) was added dropwise to a mixture suspension of 3-methoxy-4-nitropyridine 1-oxide (9.54 g, 56.1 mmol) and ethyl acetate (100 mL), at such a rate that the temperature of the reaction system did not exceed 40° C. After the dropwise addition, the resultant mixture was stirred at that temperature for 10 minutes, subsequently heated to the temperature at which the solvent was refluxed, and then stirred at this temperature for 17 hours. The reaction mixture was allowed to cool to room temperature and then poured into ice water (500 mL). This mixture was separated, and the aqueous layer obtained was cooled with ice. Sodium hydroxide was added thereto with cooling with ice at such a rate that the temperature of the reaction system did not exceed 20° C., thereby adjusting the pH of the reaction system to 10 or higher. The reaction mixture was extracted with ethyl acetate, the organic layer was washed with brine, and anhydrous sodium sulfate was added to dry the layer. After anhydrous sodium sulfate was removed by filtration, the solvent was distilled off under reduced pressure. The residue was purified by flash chromatography to obtain 4-bromo-3-methoxypyridine. The 4-bromo-3-methoxypyridine obtained was dissolved in 100 mL of ethyl acetate, and a 1.0M hydrogen chloride ether solution (60 mL, 60 mmol) was added to the resultant solution. The solvent was distilled off under reduced pressure to obtain 4-bromo-3-methoxypyridine hydrochloride (7.80 g; yield, 62%).

(3) Synthesis of the Desired Substance

The 4-bromo-3-methoxypyridine hydrochloride (4.8 g, 21.4 mmol), 4-tert-butylphenylacetylene (5.1 g, 32.1 mmol), copper(I) iodide (0.68 g, 3.2 mmol), bis(triphenylphosphine) palladium(II) dichloride (0.75 g, 1.1 mmol), triethylamine (12 mL, 85.5 mmol), and N,N-dimethylformamide (100 mL) were reacted at 60° C. for 15 hours in a nitrogen atmosphere. After the reaction mixture was allowed to cool to room temperature, water was added thereto, followed by extracting with ethyl acetate. The organic layer was washed with water and brine, and anhydrous sodium sulfate was added to dry the layer. After anhydrous sodium sulfate was removed by filtration, the organic layer was concentrated under reduced pressure and the residue was purified by silica gel column chromatography (eluent: n-heptane/ethyl acetate=67/33 by volume) to obtain the desired substance (3.2 g; yield, 56%) as a solid.

Synthesis Example 11

Synthesis of 4-((4-tert-butyl)phenyl)ethynyl)-3-(methoxymethyl)pyridine (Compound No. 46)

(1) Synthesis of 4-bromo-3-(methoxymethyl)pyridine

To a mixture solution of (4-bromopyridin-3-yl)methanol (304 mg, 1.62 mmol) and tetrahydrofuran (10 mL) was added 60% sodium hydride (434 mg, 10.9 mmol) with cooling with ice. This mixture was stirred for 10 minutes with cooling with ice, subsequently heated to room temperature, and then stirred for 7 hours at the temperature. After the reaction mixture was cooled with ice, methyl iodide (0.11 mL, 1.78 mmol) was added thereto. This mixture was heated to room temperature and stirred for 7 hours at the temperature. After the mixture was cooled with ice, water (20 mL) was added thereto, followed by extracting with ethyl acetate. The organic layer was washed with brine, and anhydrous sodium sulfate was added to dry the layer. After anhydrous sodium sulfate was removed by filtration, the solvent was distilled off under reduced pressure and the residue was purified by flash chromatography to obtain 4-bromo-3-(methoxymethyl)pyridine (275 mg; yield, 84%).

(2) Synthesis of the Desired Substance 4-bromo-3-(methoxymethyl)pyridine (275 mg, 1.36 mmol), 4-tert-butylphenylacetylene (247 mg, 1.56 mmol), triethylamine (0.6 mL, 4.3 mmol), bis(triphenylphosphine) palladium(II) dichloride (48 mg, 0.07 mmol), copper(I) iodide (20 mg, 0.11 mmol), and N,N-dimethylformamide (4 mL) were reacted at 80° C. for 11 hours in a nitrogen atmosphere. After the reaction mixture was allowed to cool to room temperature, water was added thereto, followed by extracting with ethyl acetate. The organic layer was washed with brine, and anhydrous sodium sulfate was added to dry the layer. After anhydrous sodium sulfate was removed by filtration, the solvent was distilled off under reduced pressure and the residue was purified by silica gel column chromatography (eluent: n-heptane/ethyl acetate=85/15 by volume) to obtain the desired substance (219 mg; yield, 58%).

Synthesis Example 12

Synthesis of 4-((4-tert-butylphenyl)ethynyl)-N-ethylpyridine-3-amine (Compound No. 112)

(1) Synthesis of tert-butyl (4-((4-tert-butylphenyl)ethynyl)pyridin-3-yl)carbamate Tetrahydrofuran (50 mL) and a 1.0M tetrahydrofuran solution of sodium bis(trimethylsilyl)amide (24 mL) were added to 4-((4-tert-butylphenyl)ethynyl)pyridine-3-amine (2.5 g, 10 mmol) with cooling with ice, followed by stirring for 10 minutes with ice cooling. This reaction solution was heated to room temperature and then stirred for 1 hour at the temperature. The reaction solution was cooled with ice again, and di-tert-butyl dicarbonate (2.6 g, 11.9 mmol) was added thereto, followed by stirring for 15 minutes. This reaction solution was heated to room temperature and then stirred for 4 hours at the temperature. The reaction mixture was added to an aqueous ammonium chloride solution, followed by extracting with ethyl acetate. The organic layer was washed with brine, and anhydrous sodium sulfate was added to dry the layer. After anhydrous sodium sulfate was removed by filtration, the organic layer was concentrated under reduced pressure and the residue was purified by silica gel column chromatography (eluent: n-heptane/ethyl acetate=90/10 by volume) to obtain amorphous tert-butyl (4-((4-tert-butylphenyl)ethynyl)pyridin-3-yl)carbamate (0.87 g; yield, 25%).

(2) Synthesis of tert-butyl (4-((4-tert-butylphenyl)ethynyl)pyridin-3-yl)(ethyl)carbamate To tert-butyl (4-((4-tert-butylphenyl)ethynyl)pyridin-3-yl)carbamate (200 mg, 0.57 mmol) were added N,N-dimethylformamide (10 mL), ethyl iodide (180 mg, 1.15 mmol), and 60% sodium hydride (48 mg, 1.2 mmol), followed by stirring at room temperature for 2 hours and 30 minutes. The reaction mixture was added to water, followed by extracting with ethyl acetate. The organic layer was washed with brine, and anhydrous sodium sulfate was added to dry the layer. After anhydrous sodium sulfate was removed by filtration, the organic layer was concentrated under reduced pressure and the residue was purified by silica gel column chromatography (eluent: n-heptane/ethyl acetate=95/5 by volume) to obtain amorphous tert-butyl (4-((4-tert-butylphenyl)ethynyl)pyridin-3-yl)(ethyl)carbamate (190 mg; yield, 88%).

(3) Synthesis of the Desired Substance

To tert-butyl (4-((4-tert-butylphenyl)ethynyl)pyridin-3-yl)(ethyl)carbamate (130 mg, 0.34 mmol) were added ethyl acetate (5 mL) and 10% hydrochloric acid (5 mL), followed by stirring at 60° C. for 1 hour. After the reaction solution was allowed to cool to room temperature, this mixture was neutralized by adding an aqueous sodium hydroxide solution thereto, and was then extracted with ethyl acetate. The organic layer was washed with brine, and anhydrous sodium sulfate was added to dry the layer. After anhydrous sodium sulfate was removed by filtration, the organic layer was concentrated under reduced pressure and the residue was purified by silica gel column chromatography (eluent: n-heptane/ethyl acetate=85/15 by volume) to obtain the desired substance (73 mg; yield, 77%) as a solid.

Next, representative examples of the compound according to the present invention are enumerated in TABLE 1. These compounds can be synthesized on the basis of the Synthesis Examples given above or the various production processes described above. In TABLE 1, the numerals given in the column Property indicates the melting points (° C.), and the compounds indicated by "NMR" are compounds $^1$H-NMR spectral data of which are given in TABLE 2 and TABLE 3. In TABLE 1, TABLE 2 and TABLE 3, "No." indicates compound number. Furthermore, in the tables, Me represents a methyl group, Et represents an ethyl group, n-Pr represents a normal propyl group, i-Pr represents an isopropyl group, cyc-Pr represents a cyclopropyl group, n-Bu represents a normal butyl group, i-Bu represents an isobutyl group, sec-Bu represents a secondary butyl group, tert-Bu represents a tertiary butyl group, n-Pen represents a normal pentyl group, i-Pen represents an isopentyl group, cyc-Pen represents a cyclopentyl group, neo-Pen represents a neopentyl group, n-Hex represents a normal hexyl group, neo-Hex represents a neohexyl group, and cyc-Hex represents a cyclohexyl group. With respect to the column $R^1$, "4-F", for example, means that the compound indicated thereby has been substituted with $R^1$ only at the indicated position among the substitution positions on the chemical structural formula given in the table, that is, the compound has been substituted with a fluorine atom only at the 4-position; and "2,4-$F_2$" means that the compound indicated thereby has been substituted with fluorine atoms at the 2-position and the 4-position. The same applies to the other like expressions. When the compound was in the form of a salt, the name of the salt was described in the "Remarks".

General Formula (I):

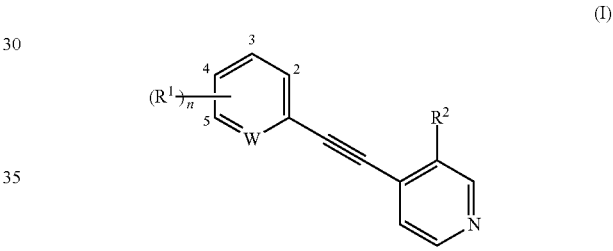

(I)

TABLE 1

| No. | $R^1$ | $R^2$ | W | n | Property | Remarks |
|---|---|---|---|---|---|---|
| 1 | 4-F | $CH_2CH=CH_2$ | CH | 1 | | NMR |
| 2 | 4-Cl | $CH_2CH=CH_2$ | CH | 1 | | |
| 3 | 4-Br | $CH_2CH=CH_2$ | CH | 1 | | |
| 4 | 4-I | $CH_2CH=CH_2$ | CH | 1 | | |
| 5 | 4-$NO_2$ | $CH_2CH=CH_2$ | CH | 1 | | NMR |
| 6 | 4-CN | $CH_2CH=CH_2$ | CH | 1 | | |
| 7 | 4-Me | $CH_2CH=CH_2$ | CH | 1 | | NMR |
| 8 | 4-tert-Bu | F | CH | 1 | 91 | |
| 9 | 4-tert-Bu | Cl | CH | 1 | | NMR |
| 10 | 4-tert-Bu | Br | CH | 1 | 109 | |
| 11 | 4-tert-Bu | I | CH | 1 | | |
| 12 | 4-tert-Bu | CN | CH | 1 | | NMR |
| 13 | 4-tert-Bu | $NO_2$ | CH | 1 | | NMR |
| 14 | 4-tert-Bu | Me | CH | 1 | | NMR |
| 15 | 4-tert-Bu | n-Pr | CH | 1 | | NMR |
| 16 | 4-tert-Bu | n-Bu | CH | 1 | | |
| 17 | 4-tert-Bu | $CH_2CH=CH_2$ | CH | 1 | | NMR |
| 18 | 4-tert-Bu | $CH_2C\equiv CH$ | CH | 1 | | |
| 19 | 4-tert-Bu | $CF_3$ | CH | 1 | | NMR |
| 20 | 4-tert-Bu | OH | CH | 1 | 142 | |
| 21 | 4-tert-Bu | OMe | CH | 1 | 93 | |
| 22 | 4-tert-Bu | O—n-Pr | CH | 1 | | NMR |
| 23 | 4-tert-Bu | $OCH_2CH=CH_2$ | CH | 1 | | |
| 24 | 4-tert-Bu | $OCH_2C\equiv CH$ | CH | 1 | | |
| 25 | 4-tert-Bu | SH | CH | 1 | | |
| 26 | 4-tert-Bu | SMe | CH | 1 | | NMR |
| 27 | 4-tert-Bu | S—n-Pr | CH | 1 | | NMR |
| 28 | 4-tert-Bu | $SCH_2CH=CH_2$ | CH | 1 | | NMR |

TABLE 1-continued

| No. | R$^1$ | R$^2$ | W | n | Property | Remarks |
|---|---|---|---|---|---|---|
| 29 | 4-tert-Bu | SCH$_2$C≡CH | CH | 1 | | |
| 30 | 4-tert-Bu | NH$_2$ | CH | 1 | 149 | |
| 31 | 4-tert-Bu | NHMe | CH | 1 | 161 | |
| 32 | 4-tert-Bu | NH—n-Pr | CH | 1 | | NMR |
| 33 | 4-tert-Bu | NHCH$_2$CH=CH$_2$ | CH | 1 | | NMR |
| 34 | 4-tert-Bu | NHCH$_2$C≡CH | CH | 1 | 130 | |
| 35 | 4-tert-Bu | N(CH$_2$CH=CH$_2$)$_2$ | CH | 1 | | NMR |
| 36 | 4-tert-Bu | N(CH$_2$C≡CH)$_2$ | CH | 1 | 117 | |
| 37 | 4-tert-Bu | SOMe | CH | 1 | | NMR |
| 38 | 4-tert-Bu | SO—n-Pr | CH | 1 | | |
| 39 | 4-tert-Bu | SOCH$_2$CH=CH$_2$ | CH | 1 | 69 | |
| 40 | 4-tert-Bu | SOCH$_2$C≡CH | CH | 1 | | |
| 41 | 4-tert-Bu | SO$_2$Me | CH | 1 | | NMR |
| 42 | 4-tert-Bu | SO$_2$—n-Pr | CH | 1 | | NMR |
| 43 | 4-tert-Bu | SO$_2$CH$_2$CH=CH$_2$ | CH | 1 | 144 | |
| 44 | 4-tert-Bu | SO$_2$CH$_2$C≡CH | CH | 1 | | |
| 45 | 4-tert-Bu | CH$_2$OH | CH | 1 | | NMR |
| 46 | 4-tert-Bu | CH$_2$OMe | CH | 1 | 82 | |
| 47 | 4-tert-Bu | CH$_2$SMe | CH | 1 | | NMR |
| 48 | 4-tert-Bu | CH$_2$NHMe | CH | 1 | | NMR |
| 49 | 4-tert-Bu | CH$_2$NMe$_2$ | CH | 1 | | NMR |
| 50 | 4-tert-Bu | CHO | CH | 1 | | NMR |
| 51 | 4-tert-Bu | CO$_2$H | CH | 1 | 101 | |
| 52 | 4-tert-Bu | CO$_2$Et | CH | 1 | | NMR |
| 53 | 4-tert-Bu | COEt | CH | 1 | | NMR |
| 54 | 4-tert-Bu | CONHMe | CH | 1 | | NMR |
| 55 | 4-tert-Bu | CONMe$_2$ | CH | 1 | | |
| 56 | 4-tert-Bu | OCOMe | CH | 1 | | NMR |
| 57 | 4-tert-Bu | SCOMe | CH | 1 | | |
| 58 | 4-tert-Bu | NHCOMe | CH | 1 | | NMR |
| 59 | 4-tert-Bu | NHCOEt | CH | 1 | | NMR |
| 60 | 4-tert-Bu | N(COEt)$_2$ | CH | 1 | | NMR |
| 61 | 4-tert-Bu | NHCO—i-Pr | CH | 1 | | NMR |
| 62 | 4-tert-Bu | N(CO—i-Pr)$_2$ | CH | 1 | 123 | |
| 63 | 4-n-Bu | CH$_2$CH=CH$_2$ | CH | 1 | | NMR |
| 64 | 4-cyc-Pr | CH$_2$CH=CH$_2$ | CH | 1 | | |
| 65 | 4-CF$_3$ | CH$_2$CH=CH$_2$ | CH | 1 | | NMR |
| 66 | 4-OH | CH$_2$CH=CH$_2$ | CH | 1 | | |
| 67 | 4-OMe | CH$_2$CH=CH$_2$ | CH | 1 | | NMR |
| 68 | 4-O—i-Pr | CH$_2$CH=CH$_2$ | CH | 1 | | NMR |
| 69 | 4-O—tert-Bu | CH$_2$CH=CH$_2$ | CH | 1 | | NMR |
| 70 | 4-O—sec-Bu | CH$_2$CH=CH$_2$ | CH | 1 | | NMR |
| 71 | 4-O—i-Bu | CH$_2$CH=CH$_2$ | CH | 1 | | NMR |
| 72 | 4-O—cyc-Pr | CH$_2$CH=CH$_2$ | CH | 1 | | |
| 73 | 4-OCH$_2$CH=CH$_2$ | CH$_2$CH=CH$_2$ | CH | 1 | | |
| 74 | 4-OCH$_2$C≡CH | CH$_2$CH=CH$_2$ | CH | 1 | | |
| 75 | 4-OCF$_3$ | CH$_2$CH=CH$_2$ | CH | 1 | | NMR |
| 76 | 4-OCH$_2$CF$_3$ | CH$_2$CH=CH$_2$ | CH | 1 | | |
| 77 | 4-OCF(CF$_3$)$_2$ | CH$_2$CH=CH$_2$ | CH | 1 | | |
| 78 | 4-SH | CH$_2$CH=CH$_2$ | CH | 1 | | |
| 79 | 4-SMe | CH$_2$CH=CH$_2$ | CH | 1 | | NMR |
| 80 | 4-S—i-Pr | CH$_2$CH=CH$_2$ | CH | 1 | | |
| 81 | 4-S(O)Me | CH$_2$CH=CH$_2$ | CH | 1 | | |
| 82 | 4-S(O)—i-Pr | CH$_2$CH=CH$_2$ | CH | 1 | | |
| 83 | 4-S(O)$_2$Me | CH$_2$CH=CH$_2$ | CH | 1 | | |
| 84 | 4-S(O)$_2$—i-Pr | CH$_2$CH=CH$_2$ | CH | 1 | | |
| 85 | 4-NH$_2$ | CH$_2$CH=CH$_2$ | CH | 1 | | NMR |
| 86 | 4-NHMe | CH$_2$CH=CH$_2$ | CH | 1 | | |
| 87 | 4-NH—i-Pr | CH$_2$CH=CH$_2$ | CH | 1 | | |
| 88 | 4-NMe$_2$ | CH$_2$CH=CH$_2$ | CH | 1 | | NMR |
| 89 | 4-CO$_2$H | CH$_2$CH=CH$_2$ | CH | 1 | | |
| 90 | 4-CO$_2$Me | CH$_2$CH=CH$_2$ | CH | 1 | | |
| 91 | 4-CO$_2$Et | CH$_2$CH=CH$_2$ | CH | 1 | | |
| 92 | 4-COMe | CH$_2$CH=CH$_2$ | CH | 1 | 56 | |
| 93 | 4-CONHMe | CH$_2$CH=CH$_2$ | CH | 1 | | |
| 94 | 4-CONMe$_2$ | CH$_2$CH=CH$_2$ | CH | 1 | | |
| 95 | 4-OCOMe | CH$_2$CH=CH$_2$ | CH | 1 | | |
| 96 | 4-NHCOMe | CH$_2$CH=CH$_2$ | CH | 1 | | |
| 97 | 4-NMeCOMe | CH$_2$CH=CH$_2$ | CH | 1 | | |
| 98 | 2-CF$_3$ | CH$_2$CH=CH$_2$ | CH | 1 | | NMR |
| 99 | 3-CF$_3$ | CH$_2$CH=CH$_2$ | CH | 1 | | NMR |
| 100 | 2,4-F$_2$ | CH$_2$CH=CH$_2$ | CH | 2 | | NMR |
| 101 | 2-NO$_2$-4-tert-Bu | CH$_2$CH=CH$_2$ | CH | 2 | | NMR |
| 102 | 2-NH$_2$-4-tert-Bu | CH$_2$CH=CH$_2$ | CH | 2 | | |
| 103 | 2-Cl-4-tert-Bu | CH$_2$CH=CH$_2$ | CH | 2 | | |
| 104 | 2-Br-4-tert-Bu | CH$_2$CH=CH$_2$ | CH | 2 | | |
| 105 | 2-F-4-O—i-Pr | CH$_2$CH=CH$_2$ | CH | 2 | | NMR |
| 106 | 2,6-F$_2$-4-O—i-Pr | CH$_2$CH=CH$_2$ | CH | 3 | | |

TABLE 1-continued

| No. | R¹ | R² | W | n | Property | Remarks |
|---|---|---|---|---|---|---|
| 107 | 3-F-4-O—i-Pr | $CH_2CH=CH_2$ | CH | 2 | NMR | |
| 108 | 3-Cl-4-O—i-Pr | $CH_2CH=CH_2$ | CH | 2 | | |
| 109 | 4-$CF_3$ | $CH_2CH=CH_2$ | N | 1 | NMR | |
| 110 | 2-Cl-4-$CF_3$ | $CH_2CH=CH_2$ | N | 2 | | |
| 111 | 4-tert-Bu | $NMe_2$ | CH | 1 | NMR | |
| 112 | 4-tert-Bu | NHEt | CH | 1 | 90 | |
| 113 | 4-tert-Bu | NH—n-Bu | CH | 1 | 81 | |
| 114 | 4-tert-Bu | NH—n-Pen | CH | 1 | 102 | |
| 115 | 4-tert-Bu | NH—n-Hex | CH | 1 | 73 | |
| 116 | 4-tert-Bu | NH—i-Pr | CH | 1 | 76 | |
| 117 | 4-tert-Bu | NH—i-Bu | CH | 1 | 73 | |
| 118 | 4-tert-Bu | S—i-Pr | CH | 1 | NMR | |
| 119 | 4-tert-Bu | S—i-Bu | CH | 1 | NMR | |
| 120 | 4-tert-Bu | OEt | CH | 1 | NMR | |
| 121 | 4-tert-Bu | O—i-Pr | CH | 1 | NMR | |
| 122 | 4-tert-Bu | O—i-Bu | CH | 1 | NMR | |
| 123 | 4-tert-Bu | O—n-Pent | CH | 1 | NMR | |
| 124 | 4-CH=C($CH_3$)$_2$ | OMe | CH | 1 | NMR | |
| 125 | 4-C≡C-tert-Bu | OMe | CH | 1 | NMR | |
| 126 | 4-Me | OMe | CH | 1 | NMR | |
| 127 | 4-$CF_3$ | OMe | CH | 1 | NMR | |
| 128 | 4-F | OMe | CH | 1 | 63 | |
| 129 | 4-O—i-Pr | OMe | CH | 1 | 107 | |
| 130 | 4-O—sec-Bu | OMe | CH | 1 | NMR | |
| 131 | 4-O—tert-Bu | OMe | CH | 1 | 69 | |
| 132 | 4-O—neo-Pen | OMe | CH | 1 | NMR | |
| 133 | 4-$OCF_3$ | OMe | CH | 1 | NMR | |
| 134 | 4-O—cyc-Pen | OMe | CH | 1 | NMR | |
| 135 | 4-S—tert-Bu | OMe | CH | 1 | NMR | |
| 136 | 4-$SCF_3$ | OMe | CH | 1 | 94 | |
| 137 | 4-COOMe | OMe | CH | 1 | 143 | |
| 138 | 3-tert-Bu | OMe | CH | 1 | NMR | |
| 139 | 4-O—tert-Bu | OEt | CH | 1 | NMR | |
| 140 | 4-O—n-Pr | $CH_2CH=CH_2$ | CH | 1 | NMR | |
| 141 | 4-O—CH($CH_2CH_3$)$_2$ | $CH_2CH=CH_2$ | CH | 1 | NMR | |
| 142 | 4-O—CH=$CH_2$ | $CH_2CH=CH_2$ | CH | 1 | NMR | |
| 143 | 4-CF($CF_3$)$_2$ | $CH_2CH=CH_2$ | CH | 1 | NMR | |
| 144 | 3-tert-Bu | $CH_2CH=CH_2$ | CH | 1 | NMR | |
| 145 | 3-O—i-Pr | $CH_2CH=CH_2$ | CH | 1 | NMR | |
| 146 | 3-O—sec-Bu | $CH_2CH=CH_2$ | CH | 1 | NMR | |
| 147 | 3-O—i-Bu | $CH_2CH=CH_2$ | CH | 1 | NMR | |
| 148 | 3-O—i-Pen | $CH_2CH=CH_2$ | CH | 1 | NMR | |
| 149 | 3,4-(MeO)$_2$ | $CH_2CH=CH_2$ | CH | 2 | NMR | |
| 150 | 3,5-(MeO)$_2$ | $CH_2CH=CH_2$ | CH | 2 | NMR | |
| 151 | 3,5-(tert-Bu)$_2$ | $CH_2CH=CH_2$ | CH | 2 | NMR | |
| 152 | 3-Me-4-O—i-Pr | $CH_2CH=CH_2$ | CH | 2 | NMR | |
| 153 | 4-tert-Bu | $CH_2OEt$ | CH | 1 | NMR | |
| 154 | 4-$CF_3$ | NHEt | CH | 1 | 89 | |
| 155 | 4-tert-Bu | OMe | CH | 1 | 164 | hydrochloride |
| 156 | 4-tert-Bu | CH(OH)$CH_2CH_3$ | CH | 1 | NMR | |
| 157 | 4-tert-Bu | $CH_2CH=CH_2$ | CH | 1 | NMR | hydrochloride |
| 158 | 4-S—cyc-Pen | OMe | CH | 1 | NMR | |
| 159 | 4-F | CH=$CHCH_3$ | CH | 1 | NMR | |
| 160 | 4-$OCF_3$ | CH=$CHCH_3$ | CH | 1 | NMR | |
| 161 | 4-neo-Hex | OMe | CH | 1 | | |
| 162 | 4-cyc-Hex | OMe | CH | 1 | 110 | |
| 163 | 4-SMe | OMe | CH | 1 | 101 | |
| 164 | 4-SOMe | OMe | CH | 1 | | |
| 165 | 4-$SO_2$Me | OMe | CH | 1 | 152 | |
| 166 | 4-CN | OMe | CH | 1 | 88 | |
| 167 | 4-NH—i-Pr | OMe | CH | 1 | 145 | |
| 168 | 4-CONHMe | OMe | CH | 1 | | |
| 169 | 4-CONMe$_2$ | OMe | CH | 1 | | |
| 170 | 4-NHCOMe | OMe | CH | 1 | 181 | |
| 171 | 4-NMeCOMe | OMe | CH | 1 | 172 | |
| 172 | 4-OCOMe | OMe | CH | 1 | | |
| 173 | 4-O—tert-Bu | OMe | CH | 1 | 130 | hydrochloride |
| 174 | 4-tert-Bu | OEt | CH | 1 | 194 | hydrochloride |
| 175 | 4-O—tert-Bu | OEt | CH | 1 | 141 | hydrochloride |
| 176 | 4-$CF_3$ | OEt | CH | 1 | NMR | |
| 177 | 4-$OCF_3$ | OEt | CH | 1 | 52 | |
| 178 | 4-$SCF_3$ | OEt | CH | 1 | 92 | |
| 179 | 4-Me | OEt | CH | 1 | NMR | |
| 180 | 4-F | OEt | CH | 1 | NMR | |
| 181 | 2-SEt-4-$CF_3$ | OEt | CH | 2 | | |
| 182 | 2-S(O)Et-4-$CF_3$ | OEt | CH | 2 | | |
| 183 | 2-S(O)$_2$Et-4-$CF_3$ | OEt | CH | 2 | | |
| 184 | 4-Me | O—n-Pr | CH | 1 | NMR | |

TABLE 1-continued

| No. | R¹ | R² | W | n | Property | Remarks |
|---|---|---|---|---|---|---|
| 185 | 4-tert-Bu | O—n-Pr | CH | 1 | 196 | hydrochloride |
| 186 | 4-O—tert-Bu | O—n-Pr | CH | 1 | NMR | |
| 187 | 4-O—tert-Bu | O—n-Pr | CH | 1 | 141 | hydrochloride |
| 188 | 4-CF₃ | O—n-Pr | CH | 1 | NMR | |
| 189 | 4-OCF₃ | O—n-Pr | CH | 1 | NMR | |
| 190 | 4-SCF₃ | O—n-Pr | CH | 1 | 99 | |
| 191 | 4-F | O—n-Pr | CH | 1 | NMR | |
| 192 | 4-tert-Bu | CH₂OMe | CH | 1 | 134 | hydrochloride |
| 193 | 4-O—tert-Bu | CH₂OMe | CH | 1 | NMR | |
| 194 | 4-O—tert-Bu | CH₂OMe | CH | 1 | | hydrochloride |
| 195 | 4-CF₃ | CH₂OMe | CH | 1 | NMR | |
| 196 | 4-OCF₃ | CH₂OMe | CH | 1 | NMR | |
| 197 | 4-SCF₃ | CH₂OMe | CH | 1 | NMR | |
| 198 | 4-Me | CH₂OMe | CH | 1 | NMR | |
| 199 | 4-F | CH₂OMe | CH | 1 | NMR | |
| 200 | 4-tert-Bu | CH₂OEt | CH | 1 | 74 | hydrochloride |
| 201 | 4-O—tert-Bu | CH₂OEt | CH | 1 | NMR | |
| 202 | 4-O—tert-Bu | CH₂OEt | CH | 1 | | hydrochloride |
| 203 | 4-CF₃ | CH₂OEt | CH | 1 | NMR | |
| 204 | 4-OCF₃ | CH₂OEt | CH | 1 | NMR | |
| 205 | 4-SCF₃ | CH₂OEt | CH | 1 | NMR | |
| 206 | 4-Me | CH₂OEt | CH | 1 | NMR | |
| 207 | 4-F | CH₂OEt | CH | 1 | NMR | |
| 208 | 4-tert-Bu | CH₂O—i-Pr | CH | 1 | | |
| 209 | 4-tert-Bu | CH₂O—n-Pr | CH | 1 | NMR | |
| 210 | 4-tert-Bu | CH₂O—i-Bu | CH | 1 | | |
| 211 | 4-tert-Bu | SEt | CH | 1 | NMR | |
| 212 | 4-tert-Bu | CH₂Cl | CH | 1 | 177 | hydrochloride |
| 213 | 3-tert-Bu | NO₂ | CH | 1 | NMR | |
| 214 | 4-O—tert-Bu | NO₂ | CH | 1 | NMR | |
| 215 | 4-O—sec-Bu | NO₂ | CH | 1 | NMR | |
| 216 | 4-S—tert-Bu | NO₂ | CH | 1 | | |
| 217 | 4-S—sec-Bu | NO₂ | CH | 1 | | |
| 218 | 4-Me | NH₂ | CH | 1 | 254 | |
| 219 | 3-tert-Bu | NH₂ | CH | 1 | NMR | |
| 220 | 4-O—tert-Bu | NH₂ | CH | 1 | NMR | |
| 221 | 4-O—sec-Bu | NH₂ | CH | 1 | | |
| 222 | 4-S—tert-Bu | NH₂ | CH | 1 | | |
| 223 | 4-S—sec-Bu | NH₂ | CH | 1 | | |
| 224 | 4-Me | NHEt | CH | 1 | NMR | |
| 225 | 4-tert-Bu | NHEt | CH | 1 | 154 | hydrochloride |
| 226 | 3-tert-Bu | NHEt | CH | 1 | NMR | |
| 227 | 4-S—sec-Bu | NHEt | CH | 1 | | |
| 228 | 4-S—tert-Bu | NHEt | CH | 1 | | |
| 229 | 4-Et | NHEt | CH | 1 | | |
| 230 | 4-n-Pr | NHEt | CH | 1 | | |
| 231 | 4-n-Bu | NHEt | CH | 1 | | |
| 232 | 4-F | NHEt | CH | 1 | | |
| 233 | 4-OMe | NHEt | CH | 1 | | |
| 234 | 4-OCF₃ | NHEt | CH | 1 | | |
| 235 | 4-O—sec-Bu | NHEt | CH | 1 | | |
| 236 | 4-O—tert-Bu | NHEt | CH | 1 | | |
| 237 | 2-SEt-4-CF₃ | NHEt | CH | 2 | | |
| 238 | 2-S(O)Et-4-CF₃ | NHEt | CH | 2 | | |
| 239 | 2-S(O)₂Et-4-CF₃ | NHEt | CH | 2 | | |
| 240 | 4-tert-Bu | N(Me)Et | CH | 1 | NMR | |
| 241 | 4-tert-Bu | Et | CH | 1 | NMR | |
| 242 | 4-OMe | CH₂OMe | N | 1 | | |
| 243 | 4-OEt | CH₂OMe | N | 1 | | |
| 244 | 4-O—n-Pr | CH₂OMe | N | 1 | | |
| 245 | 4-O—i-Pr | CH₂OMe | N | 1 | NMR | |
| 246 | 4-O—tert-Bu | CH₂OMe | N | 1 | | |
| 247 | 4-OMe | CH₂OEt | N | 1 | | |
| 248 | 4-OEt | CH₂OEt | N | 1 | | |
| 249 | 4-O—n-Pr | CH₂OEt | N | 1 | | |
| 250 | 4-O—i-Pr | CH₂OEt | N | 1 | NMR | |
| 251 | 4-O—tert-Bu | CH₂OEt | N | 1 | | |
| 252 | 4-OMe | OMe | N | 1 | | |
| 253 | 4-OEt | OMe | N | 1 | NMR | |
| 254 | 4-O—n-Pr | OMe | N | 1 | | |
| 255 | 4-O—i-Pr | OMe | N | 1 | NMR | |
| 256 | 4-O—tert-Bu | OMe | N | 1 | | |
| 257 | 4-tert-Bu | OMe | CH | 1 | | oxalate |
| 258 | 4-tert-Bu | OMe | CH | 1 | | trifluoroacetate, |
| 259 | 4-tert-Bu | OMe | CH | 1 | | p-toluenesulfonate |
| 260 | 4-O—i-Pr | OMe | CH | 1 | | hydrochloride |
| 261 | 4-O—i-Pr | OMe | CH | 1 | | oxalate |
| 262 | 4-O—i-Pr | OMe | CH | 1 | | trifluoroacetate, |

TABLE 1-continued

| No. | R¹ | R² | W | n | Property | Remarks |
|---|---|---|---|---|---|---|
| 263 | 4-O—i-Pr | OMe | CH | 1 | | p-toluenesulfonate |
| 264 | 4-O—tert-Bu | OMe | CH | 1 | | oxalate |
| 265 | 4-O—tert-Bu | OMe | CH | 1 | | trifluoroacetate, |
| 266 | 4-O—tert-Bu | OMe | CH | 1 | | p-toluenesulfonate |
| 267 | 4-SCF₃ | OMe | CH | 1 | | hydrochloride |
| 268 | 4-SCF₃ | OMe | CH | 1 | | oxalate |
| 269 | 4-SCF₃ | OMe | CH | 1 | | trifluoroacetate, |
| 270 | 4-SCF₃ | OMe | CH | 1 | | p-toluenesulfonate |
| 271 | 4-tert-Bu | OEt | CH | 1 | | oxalate |
| 272 | 4-tert-Bu | OEt | CH | 1 | | trifluoroacetate, |
| 273 | 4-tert-Bu | OEt | CH | 1 | | p-toluenesulfonate |
| 274 | 4-O—tert-Bu | OEt | CH | 1 | | oxalate |
| 275 | 4-O—tert-Bu | OEt | CH | 1 | | trifluoroacetate, |
| 276 | 4-O—tert-Bu | OEt | CH | 1 | | p-toluenesulfonate |
| 277 | 4-OCF₃ | OEt | CH | 1 | | hydrochloride |
| 278 | 4-OCF₃ | OEt | CH | 1 | | oxalate |
| 279 | 4-OCF₃ | OEt | CH | 1 | | trifluoroacetate, |
| 280 | 4-OCF₃ | OEt | CH | 1 | | p-toluenesulfonate |
| 281 | 4-SCF₃ | OEt | CH | 1 | | hydrochloride |
| 282 | 4-SCF₃ | OEt | CH | 1 | | oxalate |
| 283 | 4-SCF₃ | OEt | CH | 1 | | trifluoroacetate, |
| 284 | 4-SCF₃ | OEt | CH | 1 | | p-toluenesulfonate |
| 285 | 4-tert-Bu | O—n-Pr | CH | 1 | 149 | oxalate |
| 286 | 4-tert-Bu | O—n-Pr | CH | 1 | 96 | trifluoroacetate, |
| 287 | 4-tert-Bu | O—n-Pr | CH | 1 | 141 | p-toluenesulfonate |
| 288 | 4-O—tert-Bu | O—n-Pr | CH | 1 | | oxalate |
| 289 | 4-O—tert-Bu | O—n-Pr | CH | 1 | | trifluoroacetate, |
| 290 | 4-O—tert-Bu | O—n-Pr | CH | 1 | | p-toluenesulfonate |
| 291 | 4-CF₃ | O—n-Pr | CH | 1 | | hydrochloride |
| 292 | 4-CF₃ | O—n-Pr | CH | 1 | | oxalate |
| 293 | 4-CF₃ | O—n-Pr | CH | 1 | | trifluoroacetate, |
| 294 | 4-CF₃ | O—n-Pr | CH | 1 | | p-toluenesulfonate |
| 295 | 4-SCF₃ | O—n-Pr | CH | 1 | | hydrochloride |
| 296 | 4-SCF₃ | O—n-Pr | CH | 1 | | oxalate |
| 297 | 4-SCF₃ | O—n-Pr | CH | 1 | | trifluoroacetate, |
| 298 | 4-SCF₃ | O—n-Pr | CH | 1 | | p-toluenesulfonate |
| 299 | 4-tert-Bu | CH₂OMe | CH | 1 | | oxalate |
| 300 | 4-tert-Bu | CH₂OMe | CH | 1 | | trifluoroacetate, |
| 301 | 4-tert-Bu | CH₂OMe | CH | 1 | | p-toluenesulfonate |
| 302 | 4-O—tert-Bu | CH₂OMe | CH | 1 | | oxalate |
| 303 | 4-O—tert-Bu | CH₂OMe | CH | 1 | | trifluoroacetate, |
| 304 | 4-O—tert-Bu | CH₂OMe | CH | 1 | | p-toluenesulfonate |
| 305 | 4-tert-Bu | Et | CH | 1 | NMR | hydrochloride |
| 306 | 4-tert-Bu | Et | CH | 1 | | oxalate |
| 307 | 4-tert-Bu | Et | CH | 1 | | trifluoroacetate, |
| 308 | 4-tert-Bu | Et | CH | 1 | | p-toluenesulfonate |
| 309 | 4-tert-Bu | n-Pr | CH | 1 | | hydrochloride |
| 310 | 4-tert-Bu | n-Pr | CH | 1 | | oxalate |
| 311 | 4-tert-Bu | n-Pr | CH | 1 | | trifluoroacetate, |
| 312 | 4-tert-Bu | n-Pr | CH | 1 | | p-toluenesulfonate |
| 313 | 4-tert-Bu | CH₂OEt | CH | 1 | | oxalate |
| 314 | 4-tert-Bu | CH₂OEt | CH | 1 | | trifluoroacetate, |
| 315 | 4-tert-Bu | CH₂OEt | CH | 1 | | p-toluenesulfonate |
| 316 | 4-tert-Bu | O—i-Pr | CH | 1 | | hydrochloride |
| 317 | 4-tert-Bu | O—i-Pr | CH | 1 | | oxalate |
| 318 | 4-tert-Bu | O—i-Pr | CH | 1 | | trifluoroacetate, |
| 319 | 4-tert-Bu | O—i-Pr | CH | 1 | | p-toluenesulfonate |
| 320 | 4-tert-Bu | NHEt | CH | 1 | | oxalate |
| 321 | 4-tert-Bu | NHEt | CH | 1 | | trifluoroacetate, |
| 322 | 4-tert-Bu | NHEt | CH | 1 | | p-toluenesulfonate |
| 323 | 4-tert-Bu | NMe₂ | CH | 1 | | hydrochloride |
| 324 | 4-tert-Bu | NMe₂ | CH | 1 | | oxalate |
| 325 | 4-tert-Bu | NMe₂ | CH | 1 | | trifluoroacetate, |
| 326 | 4-tert-Bu | NMe₂ | CH | 1 | | p-toluenesulfonate |
| 327 | 4-tert-Bu | N(Me)Et | CH | 1 | | hydrochloride |
| 328 | 4-tert-Bu | N(Me)Et | CH | 1 | | oxalate |
| 329 | 4-tert-Bu | N(Me)Et | CH | 1 | | trifluoroacetate, |
| 330 | 4-tert-Bu | N(Me)Et | CH | 1 | | p-toluenesulfonate |
| 331 | 4-tert-Bu | SEt | CH | 1 | | hydrochloride |
| 332 | 4-tert-Bu | SEt | CH | 1 | | oxalate |
| 333 | 4-tert-Bu | SEt | CH | 1 | | trifluoroacetate, |
| 334 | 4-tert-Bu | SEt | CH | 1 | | p-toluenesulfonate |
| 335 | 4-tert-Bu | S—n-Pr | CH | 1 | | hydrochloride |
| 336 | 4-tert-Bu | S—n-Pr | CH | 1 | | oxalate |
| 337 | 4-tert-Bu | S—n-Pr | CH | 1 | | trifluoroacetate, |
| 338 | 4-tert-Bu | S—n-Pr | CH | 1 | | p-toluenesulfonate |
| 339 | 4-tert-Bu | S—i-Pr | CH | 1 | | hydrochloride |
| 340 | 4-tert-Bu | S—i-Pr | CH | 1 | | oxalate |

TABLE 1-continued

| No. | R¹ | R² | W | n | Property | Remarks |
|---|---|---|---|---|---|---|
| 341 | 4-tert-Bu | S—i-Pr | CH | 1 | | trifluoroacetate, |
| 342 | 4-tert-Bu | S—i-Pr | CH | 1 | | p-toluenesulfonate |
| 343 | 4-tert-Bu | S—i-Bu | CH | 1 | | hydrochloride |
| 344 | 4-tert-Bu | S—i-Bu | CH | 1 | | oxalate |
| 345 | 4-tert-Bu | S—i-Bu | CH | 1 | | trifluoroacetate, |
| 346 | 4-tert-Bu | S—i-Bu | CH | 1 | | p-toluenesulfonate |
| 347 | 4-tert-Bu | S—sec-Bu | CH | 1 | | hydrochloride |
| 348 | 4-tert-Bu | S—sec-Bu | CH | 1 | | oxalate |
| 349 | 4-tert-Bu | S—sec-Bu | CH | 1 | | trifluoroacetate, |
| 350 | 4-tert-Bu | S—sec-Bu | CH | 1 | | p-toluenesulfonate |
| 351 | 4-tert-Bu | SCH₂CH=CH₂ | CH | 1 | | hydrochloride |
| 352 | 4-tert-Bu | SCH₂CH=CH₂ | CH | 1 | | oxalate |
| 353 | 4-tert-Bu | SCH₂CH=CH₂ | CH | 1 | | trifluoroacetate, |
| 354 | 4-tert-Bu | SCH₂CH=CH₂ | CH | 1 | | p-toluenesulfonate |

TABLE 2

| No | 1H-NMR δvalue ppm Measuring Instrument: JEOL-ECX(500 MHz), Solvent: CDCl₃ |
|---|---|
| 1 | 3.60 (2H, d), 5.14 (2H, m), 6.01 (1H, d), 7.08 (2H, d), 7.35 (1H, d), 7.53 (2H, d), 8.46 (1H, d), 8.50 (1H, s) |
| 5 | 3.63 (2H, d), 5.15 (2H, m), 6.01 (1H, m), 7.40 (1H, d), 7.70 (2H, d), 8.26 (2H, d), 8.53 (1H, s), 8.56 (1H, s) |
| 7 | 2.38 (3H, s), 3.61 (2H, d), 5.14 (2H, m), 6.02 (1H, m), 7.18 (2H, d), 7.34 (1H, d), 7.45 (2H, d), 8.45 (1H, d), 8.48 (1H, s) |
| 9 | 1.34 (9H, s), 7.43 (2H, d), 7.55 (2H, d), 7.59 (1H, br), 8.52 (1H, br), 8.70 (1H, br) |
| 12 | 1.34 (9H, s), 7.43 (2H, d), 7.55 (1H, br), 7.58 (2H, d), 8.6-9.2 (2H, br) |
| 13 | 1.34 (9H, s), 7.44 (2H, d), 7.57 (2H, d), 7.59 (1H, d), 8.77 (1H, d), 9.31 (1H, s) |
| 14 | 1.34 (9H, s), 2.65 (3H, s), 7.47 (2H, d), 7.54 (2H, d), 7.83 (1H, d), 8.50 (1H, d), 8.51 (1H, s) |
| 15 | 1.05 (3H, t), 1.34 (9H, s), 1.80 (2H, m), 2.95 (2H, t), 7.48 (2H, d), 7.54 (2H, d), 7.82 (1H, d), 8.48 (1H, d) 8.53 (1H, s) |
| 17 | 1.34 (9H, s), 3.60 (2H, d), 5.14 (2H, m), 6.00 (1H, m), 7.35 (1H, d), 7.40 (2H, d), 7.48 (2H, d), 8.45 (1H, d), 8.49 (1H, s) |
| 19 | 1.34 (9H, s), 7.42 (2H, d), 7.52 (2H, d) |
| 22 | 1.12 (3H, t), 1.33 (9H, s), 1.90 (2H, tq), 4.13 (2H, t), 7.40 (2H, d), 7.40 (1H, br), 7.49 (2H, d), 8.0-8.6 (2H, br) |
| 26 | 1.33 (9H, s), 2.59 (3H, s), 7.32 (1H, d), 7.41 (2H, d), 7.53 (2H, d), 7.35 (1H, d), 8.42 (1H, s) |
| 27 | 1.13 (3H, t), 1.34 (9H, s), 1.82 (2H, m), 3.05 (2H, t), 7.47 (2H, d), 7.57 (2H, d), 7.73 (1H, d), 8.45-8.33 (2H, m) |
| 32 | 1.04 (3H, t), 1.33 (9H, s), 1.73 (2H, m), 3.23 (2H, br), 4.61 (1H, br), 7.25 (1H, d), 7.41 (2H, d), 7.47 (2H, d), 7.91 (2H, d), 8.03 (1H, s) |
| 33 | 1.32 (9H, s), 3.94 (2H, br), 4.78 (1H, br), 5.22 (1H, d), 5.33 (1H, d), 5.96 (1H, m), 7.41 (2H, d), 7.48 (2H, d), 7.94 (1H, d), 8.02 (1H, s) |
| 35 | 1.34 (9H, s), 4.18 (4H, d), 5.29 (2H, d), 5.35 (2H, d), 5.89 (2H, m), 7.44 (2H, d), 7.49 (2H, d), 7.70 (1H, d), 7.97 (1H, d), 8.06 (1H, s) |
| 37 | 1.34 (9H, s), 2.97 (3H, s), 7.44-7.55 (5H, m), 8.74 (1H, d), 9.12 (1H, s) |
| 41 | 1.34 (9H, s), 3.32 (3H, s), 7.45 (2H, d), 7.57-7.59 (3H, m), 8.82 (1H, d), 9.25 (1H, d) |
| 42 | 1.03 (3H, t), 1.34 (9H, s), 1.79 (2H, tq), 3.45 (2H, t), 7.46 (2H, d), 7.59 (2H, d), 7.69 (1H, d), 8.86 (1H, d), 9.23 (1H, s) |
| 52 | 1.33 (9H, s), 1.43 (3H, d), 4.46 (4H, t), 7.42 (2H, d), 7.55 (2H, d) |
| 53 | 1.26 (3H, t), 1.36 (9H, s), 3.17 (2H, q), 7.42 (2H, d), 7.47-7.51 (3H, m), 8.65 (1H, d), 8.92 (1H, s) |
| 58 | 1.36 (9H, s), 2.36 (3H, s), 7.51 (2H, d), 7.56 (2H, d), 7.81 (1H, d), 8.08 (1H, S), 8.41 (1H, d), 9.86 (1H, s) |
| 59 | 1.30 (3H, t), 1.35 (9H, s), 2.53 (2H, q), 7.42-7.46 (3H, m), 7.50 (2H, d), 7.87 (1H, s), 8.36 (1H, d), 9.73 (1H, s) |
| 60 | 1.15 (6H, t), 1.32 (9H, s), 2.64 (4H, q), 7.40 (4H, br), 7.56 (1H, d), 8.48 (1H, s), 8.63 (1H, d) |
| 61 | 1.33 (6H, d), 1.34 (9H, s), 2.65 (1H, m), 7.29 (2H, d), 7.45-7.46 (3H, m), 7.96 (1H, s), 8.35 (1H, d), 9.73 (1H, s) |
| 63 | 0.93 (3H, t), 1.36 (2H, sext), 1.60 (2H, quin), 2.64 (2H, t), 3.61 (2H, d), 5.14 (2H, m), 6.02 (1H, m), 7.19 (2H, d), 7.35 (1H, d), 7.46 (2H, d), 8.45 (1H, d), 8.90 (1H, s), |
| 65 | 3.62 (2H, d), 5.14 (2H, m), 6.01 (1H, m), 7.38 (1H, d), 7.65 (4H, s), 8.50 (1H, d), 8.54(1H, s) |
| 67 | 3.59 (2H, d), 3.81 (3H, s), 5.13 (2H, m), 6.00 (1H, m), 6.89 (2H, d), 7.33 (1H, d), 7.48 (2H, d), 8.43(1H, d), 8.48(1H, s) |
| 68 | 1.35 (6H, d), 3.60 (2H, d), 4.59 (1H, d), 5.13 (2H, m), 6.01 (1H, m), 6.87 (2H, d), 7.33 (1H, d), 7.46 (2H, d), 8.43 (1H, d), 8.48 (1H, s) |
| 69 | 1.36 (9H, s), 3.60 (2H, d), 5.15 (2H, m), 6.02 (1H, m), 7.00 (2H, d), 7.34 (1H, d), 7.45 (2H, d), 8.44 (1H, d), 8.49 (1H, s) |
| 70 | 0.98 (3H, t), 1.31 (3H, d), 1.70 (2H, m), 3.60 (2H, d), 4.35 (1H, m), 5.14 (2H, m), 6.01 (1H, m), 6.88 (2H, d), 7.34 (1H, d), 7.45 (2H, d), 8.48 (2H, br) |

TABLE 2-continued

| No | 1H-NMR δvalue ppm Measuring Instrument: JEOL-ECX(500 MHz), Solvent: CDCl$_3$ |
|---|---|
| 71 | 1.03 (6H, d), 2.10 (1H, m), 3.60 (2H, d), 3.74 (2H, d), 5.14 (2H, m), 6.02 (1H, m), 6.89 (2H, d), 7.32 (1H, d), 7.47 (2H, d), 8.43 (1H, d), 8.48 (1H, s) |
| 75 | 3.60 (2H, d), 5.12 (2H, m), 6.00 (1H, m), 7.23 (2H, d), 7.36 (1H, d), 7.58 (2H, d), 8.46 (1H, d), 8.51 (1H, s) |
| 79 | 2.50 (3H, s), 3.60 (2H, d), 5.15 (2H, m), 5.98 (1H, m), 7.22 (2H, d), 7.34 (1H, d), 7.45 (2H, d), 8.44 (1H, d), 8.49 (1H, s) |
| 85 | 3.59 (2H, d), 5.15 (2H, m), 6.02 (1H, m), 6.59 (4H, m), 7.32 (3H, m), 8.41(1H, d), 8.46 (1H, s) |
| 88 | 3.01 (6H, s), 3.60 (2H, d), 5.15 (2H, m), 6.02 (1H, m), 6.67 (2H, d), 7.31 (1H, d), 7.42 (2H, d), 8.41 (1H, d), 8.45(1H, s) |
| 98 | 3.62 (2H, d), 5.11 (2H, m), 6.02 (1H, m), 7.38 (1H, d), 7.48 (1H, t), 7.55 (1H, t), 7.70 (2H, t), 8.48(1H, d), 8.53(1H, s) |
| 99 | 3.62 (2H, d), 5.16 (2H, m), 6.01 (1H, m), 7.37 (1H, d), 7.52 (1H, t), 7.65 (1H, d), 7.72 (1H, d), 7.80 (1H, s), 8.50 (1H, d), 8.54(1H, s) |
| 100 | 3.61 (2H, d), 5.12 (2H, m), 6.01 (1H, m), 6.90 (2H, d), 7.36 (1H, d), 7.50 (1H, d), 8.48 (1H, s), 8.52 (1H, s) |
| 101 | 1.38 (9H, s), 3.66 (2H, d), 5.13 (2H, m), 6.03 (1H, m), 7.41 (1H, d), 7.66 (2H, s), 8.13 (1H, s), 8.49 (1H, s), 8.53 (1H, s) |
| 105 | 1.36 (6H, d), 3.61 (2H, d), 4.56 (1H, m), 5.16 (2H, m), 6.02 (1H, m), 6.68 (2H, m), 7.35 (1H, d), 7.40 (1H, m), 8.44 (1H, d), 8.49 (1H, s) |
| 107 | 1.38 (6H, d), 3.59 (2H, d), 4.61 (1H, m), 5.14 (2H, m), 6.00 (1H, m), 6.95 (1H, m), 7.25 (2H, d), 7.34 (1H, d), 8.47 (2H, br) |
| 109 | 3.65 (2H, d), 5.15 (2H, m), 6.01 (1H, m), 7.37 (1H, d), 7.67 (1H, d), 7.96 (1H, d), 8.52 (1H, d), 8.56 (1H, s), 8.92 (1H, s) |
| 111 | 1.33 (9H, s), 3.06 (6H, s), 7.28 (1H, d), 7.39 (2H, d), 7.48 (2H, d), 8.10 (1H, d), 8.26 (1H, s) |
| 118 | 1.33 (9H, s), 1.35 (6H, d), 3.62-3.66 (1H, m), 7.36 (1H, d), 7.41 (2H, d), 7.52 (2H, d), 8.42 (1H, br), 8.62 (1H, br) |
| 119 | 1.07 (6H, d), 1.33 (9H, s), 1.89-1.94 (1H, m), 2.92 (2H, d), 7.31 (1H, d), 7.41 (2H, d), 7.52 (2H, d), 8.49 (1H, d), 8.53 (1H, s) |
| 120 | 1.33 (9H, s), 1.51 (3H, t), 4.24 (2H, q), 7.34 (1H, br), 7.39 (2H, d), 7.50 (2H, d), 8.22 (1H, br), 8.31 (1H, br) |
| 121 | 1.33 (9H, s), 1.42 (6H, d), 4.66 (1H, m), 4.38 (1H, br), 7.40 (2H, d), 7.49 (2H, d), 8.06 (1H, br), 8.27 (1H, br) |
| 122 | 1.14 (6H, d), 1.34 (9H, s), 2.27 (1H, m), 3.97 (2H, d), 7.46 (2H, d), 7.53 (2H, d), 7.78 (1H, d), 8.25 (1H, d), 8.27 (1H, s) |
| 123 | 0.94 (3H, t), 1.33 (9H, s), 1.43 (2H, qt), 1.54 (2H, tt), 1.88 (2H, tt), 4.16 (2H, t), 7.33 (1H, br), 7.37 (2H, d), 7.49 (2H, d), 8.22 (1H, br), 8.31 (1H, br) |
| 126 | 2.38 (3H, s), 4.01 (3H, s), 7.17 (2H, d), 7.42 (1H, br), 7.47 (2H, d), 8.0-8.7 (2H, br) |
| 127 | 4.03 (3H, s), 7.38 (1H, br), 7.63 (2H, d), 7.68 (2H, d), 8.29 (1H, d), 8.39 (1H, br) |
| 130 | 0.99 (3H, t), 1.31 (3H, d), 1.70 (2H, m), 4.01 (3H, s), 4.35 (1H, m), 6.87 (2H, d), 7.34 (1H, d), 7.45(2H, d), 8.24 (1H, d), 8.32 (1H, s) |
| 132 | 1.03 (9H, d), 3.60 (2H, s), 4.00 (3H, s), 6.88 (2H, d), 7.49 (2H, d) |
| 133 | 4.00 (3H, s), 7.22 (2H, d), 7.35 (1H, d), 7.60 (2H, d), 8.26 (1H, s), 8.35 (1H, s) |
| 134 | 1.76 (8H, m), 4.00 (3H, s), 4.77 (1H, m), 6.85 (2H, d), 7.33 (1H, d), 7.48 (2H, d), 8.23 (1H, d), 8.31 (1H, s) |
| 135 | 1.29 (9H, s), 4.00 (3H, s), 7.35 (1H, d), 7.53 (4H, s), 8.25 (1H, s), 8.35 (1H, s) |
| 138 | 1.31 (9H, s), 4.01 (3H, s), 7.39 (3H, m), 7.60 (1H, s), 8.25 (1H, s), 8.35 (1H, s) |
| 139 | 1.37 (9H, s), 1.48 (3H, t), 4.23 (2H, q), 6.97 (2H, d), 7.47 (2H, d) |
| 140 | 1.03 (3H, t), 1.80 (2H, sext), 3.59 (2H, d), 3.92 (2H, t), 5.14 (2H, m), 6.01 (1H, m), 6.89 (2H, d), 7.32 (1H, d), 7.44 (2H, d), 8.43 (1H, d), 8.48 (1H, s) |
| 141 | 0.88 (3H, t), 0.94 (3H, t), 1.68 (4H, m), 3.60 (2H, d), 5.15 (2H, m), 5.98 (2H, m), 6.89 (2H, d), 7.47 (3H, m), 8.41 (2H, br) |
| 142 | 3.61 (2H, d), 4.54 (1H, d), 4.86 (1H, d), 5.12 (2H, m), 6.03 (1H, m), 6.66 (1H, m), 7.01 (2H, m), 7.35 (1H, d), 7.50 (2H, d), 8.45 (1H, s), 8.50 (1H, s) |
| 143 | 3.61 (2H, d), 5.15 (2H, m), 6.00 (1H, m), 7.43 (1H, s), 7.65 (4H, m), 8.51 (2H, br) |
| 144 | 1.34 (9H, s), 3.63 (2H, d), 5.16 (2H, m), 6.03 (1H, m), 7.33 (1H, d), 7.37 (2H, d), 7.43 (1H, d), 7.57 (1H, s), 8.47 (1H, s), 8.51 (1H, s) |
| 145 | 1.35 (6H, d), 3.60 (2H, d), 4.57 (1H, m), 5.14 (2H, m), 6.01 (1H, m), 6.93 (1H, d), 7.05 (1H, s), 7.11 (1H, d), 7.27 (1H, m), 7.35 (1H, d), 8.45 (2H, br) |
| 146 | 0.99 (3H, t), 1.31 (3H, d), 1.70 (2H, m), 3.51 (2H, d), 4.33 (1H, m), 5.15 (2H, m), 5.98 (1H, m), 6.93 (1H, dd), 7.05 (1H, s), 7.11 (1H, d), 7.27 (1H, m), 7.49 (1H, d), 8.43 (2H, br) |
| 147 | 1.04 (6H, d), 2.01 (1H, m), 3.74 (2H, d), 5.15 (2H, m), 6.00 (1H, m), 6.94 (1H, d), 7.07 (1H, s), 7.12 (1H, d), 7.27 (1H, m), 8.43 (2H, br) |
| 148 | 0.97 (6H, d), 1.69 (2H, q), 1.82 (1H, m), 3.62 (2H, d), 4.01 (2H, t), 5.16 (2H, m), 6.01 (1H, m), 6.94 (1H, d), 7.06 (1H, s), 7.13 (1H, d), 7.26 (1H, m), 7.39 (1H, s), 8.49 (2H, br) |
| 149 | 3.60 (2H, d), 3.88 (3H, s), 3.89 (3H, s), 5.15 (2H, m), 6.02 (1H, m), 6.83 (1H, d), 7.03 (1H, s), 7.15 (1H, d), 7.32 (1H, d), 8.44 (1H, d), 8.49 (1H, s) |
| 150 | 3.60 (2H, d), 3.80 (6H, s), 5.14 (2H, m), 6.01 (1H, m), 6.51 (1H, d), 6.69 (2H, d), 7.35 (1H, d), 8.46 (1H, s), 8.50 (1H, s) |
| 151 | 1.32 (18H, s), 3.64 (2H, d), 5.16 (2H, m), 6.03 (1H, m), 7.39 (3H, m), 7.47 (1H, t), 8.50 (2H, br) |
| 152 | 1.36 (6H, d), 2.20 (3H, s), 3.60 (2H, d), 4.58 (1H, m), 5.15 (2H, m), 6.02 (1H, m), 6.81 (1H, d), 7.35 (3H, m), 8.42 (2H, br) |

TABLE 2-continued

| No | 1H-NMR δvalue ppm Measuring Instrument: JEOL-ECX(500 MHz), Solvent: CDCl$_3$ |
|---|---|
| 153 | 1.26 (3H, t), 1.32 (9H, s), 3.64 (2H, q), 4.72 (2H, s), 7.34 (1H, d), 7.40 (2H, m), 7.47 (2H, m), 8.50 (1H, d), 8.70 (1H, s) |
| 157 | 1.35 (9H, s), 3.71 (2H, d), 5.25 (2H, m), 5.98 (1H, m), 7.45 (2H, d), 7.53 (2H, d), 7.71 (1H, s), 8.59 (1H, br) |
| 158 | 1.61 (4H, m), 1.77 (2H, m), 2.07 (2H, m), 3.63 (1H, m), 3.98 (3H, s), 7.27 (2H, d), 7.32 (1H, d), 7.45 (2H, d), 8.22 (1H, d), 8.31 (1H, s) |
| 159 | 1.98 (3H, d), 6.48 (1H, m), 6.77 (1H, d), 7.09 (2H, m), 7.31 (1H, d), 7.55 (2H, m), 8.39 (1H, d), 8.76 (1H, s) |
| 160 | 1.98 (3H, d), 6.48 (1H, m), 6.78 (1H, d), 7.24 (2H, d), 7.32 (1H, d), 7.60 (2H, d), 8.40 (1H, d), 8.77 (1H, s) |
| 28 | 1.33 (9H, s), 3.68 (2H, d), 5.11-5.15 (2H, m), 5.86-5.91 (1H, m), 7.33 (1H, d), 7.39-7.41 (2H, m), 7.53 (2H, d), 8.38 (1H, d), 8.54 (1H, s) |
| 45 | 1.33 (9H, s), 4.92 (2H, d), 7.39 (1H, br), 7.41 (2H, d), 7.48 (2H, d), 8.55 (1H, br), 8.72 (1H, br) |
| 47 | 1.34 (9H, s), 2.07 (3H, s), 3.88 (2H, s), 7.38 (1H, d), 7.41 (2H, d), 7.51 (2H, d), 8.48 (1H, d), 8.57 (1H, s) |
| 48 | 1.33 (9H, s), 2.47 (3H, s), 3.96 (2H, s), 7.37 (1H, d), 7.41 (2H, d), 7.49 (2H, d), 8.49 (1H, d), 8.60 (1H, s) |
| 49 | 1.34 (9H, s), 2.33 (6H, s), 3.66 (2H, s), 7.37 (1H, d), 7.41 (2H, d), 7.50 (2H, d), 8.48 (1H, d), 8.64 (1H, s) |
| 50 | 1.34 (9H, s), 7.44 (2H, d), 7.49 (1H, d), 7.54 (2H, d), 8.76 (1H, d), 9.11 (1H, s), 10.64 (1H, s) |
| 54 | 1.35 (9H, s), 3.09(3H, d), 7.41-7.50 (5H, m), 8.66 (1H, br), 9.22 (1H, br) |
| 56 | 1.33 (9H, s), 2.40 (3H, s), 7.39-7.47 (5H, m), 8.44 (1H, s), 8.47 (1H, d) |
| 124 | 1.88 (3H, s), 1.92 (3H, s), 4.01 (3H, s), 6.26 (1H, s), 7.22 (2H, d), 7.36 (1H, s), 7.51 (2H, d), 8.23-8.41 (2H, br) |
| 125 | 1.30 (9H, s), 4.00 (3H, s), 7.37 (2H, d), 7.48 (2H, d) |
| 176 | 1.53 (3H, t), 4.23 (2H, q), 7.35 (1H, d), 7.64 (4H, m), 8.23 (1H, d), 8.34 (1H, s) |
| 179 | 1.51 (3H, t), 2.36 (3H, s), 4.23 (2H, q), 7.17 (2H, d), 7.33 (1H, d), 7.44 (2H, d), 8.22 (1H, s), 8.30 (1H, s) |
| 180 | 1.51 (3H, t), 4.24 (2H, q), 7.07 (2H, m), 7.34 (1H, s), 7.55 (2H, m), 8.23 (1H, s), 8.33 (1H, s) |
| 184 | 1.11 (3H, t), 1.90 (2H, sext), 4.12 (2H, t), 7.17 (2H, d), 7.33 (1H, d), 7.44 (2H, d), 8.21 (1H, s), 8.30 (1H, s) |
| 186 | 1.11 (3H, t), 1.38 (9H, s), 1.90 (2H, sext), 4.13 (2H, t), 6.98 (2H, d), 7.32 (1H, d), 7.46 (2H, d), 8.22 (1H, s), 8.30 (1H, s) |
| 188 | 1.11 (3H, t), 1.89 (2H, sext), 4.13 (2H, t), 7.35 (1H, d), 7.64 (4H, m), 8.24 (1H, s), 8.34 (1H, s) |
| 189 | 1.10 (3H, t), 1.91 (2H, sext), 4.13 (2H, t), 7.22 (2H, d), 7.34 (1H, d), 7.58 (2H, d), 8.22 (1H, s), 8.33 (1H, s) |
| 191 | 1.11 (t, 3H), 1.90 (2H, sext), 4.13 (2H, t), 7.06 (2H, m), 7.32 (1H, d), 7.54 (2H, m), 8.22 (1H, s), 8.32 (1H, s) |
| 193 | 1.38 (9H, s), 3.49 (3H, s), 4.68 (2H, s), 6.99 (2H, d), 7.36 (1H, s), 7.46 (2H, d), 8.61 (2H, br) |
| 195 | 3.50 (3H, s), 4.69 (2H, s), 7.40 (1H, d), 7.66 (4H, m), 8.57 (1H, d), 8.73 (1H, s) |
| 196 | 3.49 (3H, s), 4.68 (2H, s), 7.24 (2H, d), 7.26 (1H, s), 7.59 (2H, d), 8.60 (1H, s), 8.76 (1H, s) |
| 197 | 3.50 (3H, s), 4.68 (2H, s), 7.40 (1H, s), 7.60 (2H, d), 7.66 (2H, d), 8.61 (2H, br) |
| 198 | 2.39 (3H, s), 3.48 (3H, s), 4.69 (2H, s), 7.19 (2H, d), 7.36 (1H, d), 7.45 (2H, d), 8.53 (1H, s), 8.70 (1H, s) |
| 199 | 3.49 (3H, s), 4.68 (2H, s), 7.09 (2H, m), 7.36 (1H, d), 7.54 (2H, m), 8.54 (1H, d), 8.70 (1H, s) |
| 201 | 1.29 (3H, t), 1.38 (9H, s), 3.65 (2H, q), 4.73 (2H, s), 7.00 (2H, d), 7.35 (1H, br), 7.45 (2H, d), 8.53 (1H, br), 8.73 (1H, br) |
| 203 | 1.29 (3H, t), 3.65 (2H, q), 4.72 (2H, s), 7.38 (1H, d), 7.65 (4H, m), 8.35 (1H, d), 8.72 (1H, s) |
| 204 | 1.28 (3H, t), 3.65 (2H, q), 4.71 (2H, s), 7.24 (2H, d), 7.36 (1H, d), 7.57 (2H, d), 8.54 (1H, d), 8.72 (1H, s) |
| 205 | 1.29 (1H, t), 3.65 (2H, q), 4.71 (2H, s), 7.25 (1H, s), 7.58 (2H, d), 7.67 (2H, d), 8.55 (1H, d), 8.73 (1H, s) |
| 206 | 1.28 (3H, t), 2.39 (3H, s), 3.65 (2H, q), 4.73 (2H, s), 7.19 (2H, d), 7.36 (1H, d), 7.44 (2H, d), 8.35 (1H, br), 8.72 (1H, br) |
| 207 | 1.28 (3H, t), 3.65 (2H, q), 4.72 (2H, s), 7.06-7.11 (2H, m), 7.36 (1H, d), 7.51-7.55 (2H, m), 8.53 (1H, br), 8.72 (1H, br) |
| 209 | 0.96 (3H, t), 1.33 (9H, s), 1.67 (2H, m), 3.54 (2H, t), 4.72 (2H, s), 7.35 (1H, s), 7.41 (2H, d), 7.47 (2H, d), 8.52 (1H, br), 8.73 (1H, br) |
| 211 | 1.33 (9H, s), 1.38 (3H, t), 3.08 (2H, q), 7.32 (1H, d), 7.40 (2H, d), 7.52 (2H, d), 8.37 (1H, s), 8.52 (1H, s) |
| 213 | 1.35 (9H, s), 7.33-7.36 (1H, m), 7.45 (1H, d), 7.49 (1H, d), 7.60 (1H, d), 7.63 (1H, d), 8.77 (1H, d), 9.31 (1H, s) |
| 214 | 1.40 (9H, s), 7.01 (2H, d), 7.53-7.56 (3H, m), 8.75 (1H, d), 9.30 (1H, s) |
| 215 | 0.98 (3H, t), 1.31 (3H, d), 1.60-1.69 (1H, m), 1.72-1.79 (1H, m), 4.34-4.40 (1H, m), 6.89 (2H, d), 7.53-7.57 (3H, m), 8.73 (1H, d), 9.29 (1H, s) |

TABLE 2-continued

| No | 1H-NMR δvalue ppm Measuring Instrument: JEOL-ECX(500 MHz), Solvent: CDCl$_3$ |
|---|---|
| 219 | 1.34 (9H, s), 4.25 (2H, br), 7.20 (1H, d), 7.29-7.32 (1H, m), 7.35-7.37 (1H, m), 7.41-7.43 (1H, m), 7.55-7.56 (1H, m), 7.97 (1H, d), 8.16 (1H, s) |
| 220 | 1.38 (9H, s), 4.23 (2H, br), 6.99 (2H, d), 7.17 (1H, d), 7.45 (2H, d), 7.96 (1H, d), 8.15 (1H, s) |
| 224 | 1.33 (3H, t), 2.83 (3H, s), 3.22 (2H, q), 4.39 (1H, br), 7.16-7.19 (3H, m), 7.42 (2H, d), 7.92 (1H, d), 8.05 (1H, s) |
| 226 | 1.34 (9H, s), 1.34 (3H, t), 3.32 (2H, q), 4.41 (1H, br), 7.19 (1H, d), 7.30-7.36 (3H, m), 7.41-7.43 (1H, m), 7.93 (1H, d), 8.09 (1H, s) |
| 240 | 1.24 (3H, t), 1.32 (9H, s), 2.97 (3H, s), 4.11 (2H, q), 7.28 (1H, d), 7.38 (2H, d), 7.47 (2H, d), 8.07 (1H, d), 8.24 (1H, s) |
| 241 | 1.32 (3H, t), 1.34 (9H, s), 2.86 (2H, q), 7.33 (1H, d), 7.41 (2H, d), 7.49 (2H, d), 8.43 1H, d), 8.50 (1H, s) |
| 245 | 1.34 (6H, d), 3.46 (3H, s), 4.60 (1H, m), 4.68 (2H, s), 7.15 (2H, m), 7.44 (1H, d), 7.65 (1H, d), 8.28 (1H, d), 8.53 (1H, br), 8.70 (1H, br) |
| 250 | 1.25 (3H, t), 1.33 (6H, d), 3.62 (2H, q), 4.58 (1H, m), 4.73 (2H, s), 7.13 (1H, m), 7.37 (1H, d), 7.43 (1H, d), 8.27 (1H, d), 8.50 (1H, br), 8.70 (1H, br) |
| 253 | 1.43 (3H, t), 4.07 (3H, s), 4.08 (2H, q), 7.14 (1H, m), 7.36 (1H, d), 7.48 (1H, d), 8.22-8.31 (3H, m) |
| 255 | 1.35 (6H, d), 3.99 (3H, s), 4.59 (1H, m), 7.13 (1H, m), 7.36 (1H, d), 7.48 (1H, d), 8.22 (1H, br), 8.27 (1H, d), 8.32 (1H, br) |

TABLE 3

| No. | 1H-NMR δvalue ppm Measuring Instrument: JEOL-ECX(500 MHz), Solvent: DMSO-d$_6$ |
|---|---|
| 156 | 0.90 (3H, t), 1.28 (9H, s), 1.68 (2H, m), 4.95 (1H, m), 5.47 (1H, d), 7.50 (5H, m), 8.29 (1H, br), 8.64 (1H, br) |
| 305 | 1.29 (12H, m), 2.96 (2H, q), 7.53 (2H, d), 7.62 (2H, d), 8.09 (1H, br), 8.60-9.20 (2H, br) |

Test Example 1

Test for Examining Effect on Brown Rice Planthopper

Rice seedlings were subjected to an immersion treatment with a liquid chemical prepared so that the concentration of each Invention Compound therein was 200 ppm. After the liquid chemical was air-dried, the rice seedlings were put into a test tube, with the root portion covered with wet absorbent cotton. About 10 second- to third-instar nymphs of brown rice planthopper were released into the test tube, and the tube opening was covered with gauze. This test tube was allowed to stand in a 25° C. thermostatic chamber with illumination. On 5 days after the release of the nymphs, whether each brown rice planthopper insect was alive or dead was determined. The mortality (%) was determined using the following calculation formula. As a result, Compounds Nos. 1, 7, 8, 9, 10, 14, 15, 17, 19, 21, 22, 26, 27, 28, 30, 31, 32, 33, 35, 36, 39, 46, 53, 63, 65, 67, 68, 69, 70, 71, 75, 79, 98, 99, 100, 101, 105, 107, 111, 112, 113, 116, 117, 118, 119, 120, 121, 122, 123, 124, 125, 126, 127, 128, 129, 130, 131, 132, 133, 134, 136, 138, 139, 140, 141, 142, 143, 144, 145, 146, 147, 148, 149, 150, 151, 152, 153, 154, 155, 156, 157, 159, 160, 162, 163, 165, 167, 171, 173, 174, 175, 176, 177, 178, 179, 180, 184, 185, 186, 187, 188, 189, 190, 191, 192, 193, 197, 198, 199, 200, 201, 209, 211, 212, 224, 225, 226, 240, 241, 253, 285, 286, 287 and 305 showed a mortality of 90% or higher.

Mortality (%)=((number of dead insects)/(number of released insects))×100

Test Example 2

Test for Examining Effect on Sweet Potato Whitefly

A liquid chemical prepared so that the concentration of each Invention Compound therein was 200 ppm was sprayed, using a hand spray, on a potted cucumber seedling on which first- to second-instar nymphs of sweet potato whitefly were parasitic. After the liquid chemical was air-dried, the potted cucumber seedling was allowed to stand in a 25° C. thermostatic chamber with illumination. On 10 days after the treatment, the number of old-instar nymphs was counted and the preventive value was determined using the following calculation formula. As a result, Compounds Nos. 1, 7, 9, 10, 12, 15, 17, 19, 20, 21, 22, 26, 27, 28, 31, 32, 33, 35, 36, 39, 46, 47, 49, 51, 52, 53, 56, 58, 61, 63, 65, 67, 68, 69, 70, 71, 75, 79, 88, 100, 101, 105, 107, 109, 111, 112, 113, 116, 117, 118, 119, 120, 121, 122, 124, 126, 127, 128, 129, 130, 131, 132, 133, 135, 136, 138, 139, 140, 141, 143, 144, 149, 150, 151, 152, 153, 154, 155, 156, 157, 160, 162, 163, 165, 166, 173, 174, 175, 176, 177, 178, 179, 180, 185, 186, 187, 188, 189, 190, 191, 192, 193, 197, 199, 200, 201, 203, 204, 206, 207, 209, 211, 212, 224, 225, 226, 240, 241, 253, 255, 285, 286, 287 and 305 showed a preventive value of 90 or higher.

Preventive value=(1−(Ta×Cb)/(Tb×Ca))×100

Ta: number of old-instar nymphs in treated cucumber seedling counted after the treatment
Tb: number of first- to second-instar nymphs in treated cucumber seedling counted before the treatment
Ca: number of old-instar nymphs in untreated cucumber seedling counted after the treatment
Cb: number of first- to second-instar nymphs in untreated cucumber seedling counted before the treatment Test Example 3

Test for Examining Effect on *Haemaphysalis longicornis*

A solution prepared so that the concentration of each Invention Compound therein was 100 ppm was used to treat a plastic vial. After the liquid chemical was air-dried, young mites were placed in the vial. This vial was allowed to stand under constant dark conditions at 25° C. and a relative humidity of 80-100%. At 24 hours after the contact with the chemical, the number of dead mites was recorded. The mortality (%) was determined using the following calculation formula. As a result, Compounds Nos. 7, 15, 17, 65, 67, 68, 69, 75, 79, 99, 100, 109, 140, 159, 160, 179, 191, 196, 203, 204, 206, and 207 showed a mortality of 90% or higher.

Mortality (%)=((number of dead ticks)/(number of all ticks))×100

Formulation Examples are given below.

Formulation Example 1

(1) Invention Compound, 20 parts by weight
(2) Clay, 70 parts by weight
(3) White carbon, 5 parts by weight
(4) Sodium polycarboxylate, 3 parts by weight
(5) Sodium alkylnaphthalenesulfonate, 2 parts by weight
The above ingredients are evenly mixed to obtain a wettable powder.

Formulation Example 2

(1) Invention Compound, 5 parts by weight
(2) Talc, 60 parts by weight
(3) Calcium carbonate, 34.5 parts by weight
(4) Liquid paraffin, 0.5 parts by weight
The above ingredients are evenly mixed to obtain a dust.

Formulation Example 3

(1) Invention Compound, 20 parts by weight
(2) N,N-dimethylacetamide, 20 parts by weight
(3) Polyoxyethylene tristyrylphenyl ether, 10 parts by weight
(4) Calcium dodecylbenzenesulfonate, 2 parts by weight
(5) Xylene, 48 parts by weight
The above ingredients are evenly mixed and dissolved to obtain an emulsifiable concentrate.

Formulation Example 4

(1) Clay, 68 parts by weight
(2) Sodium ligninsulfonate, 2 parts by weight
(3) Polyoxyethylene alkylaryl sulfate, 5 parts by weight
(4) White carbon, 25 parts by weight
A mixture of the above ingredients is mixed with an Invention Compound in a weight ratio of 4:1 to obtain a wettable powder.

Formulation Example 5

(1) Invention Compound, 50 parts by weight
(2) Sodium alkylnaphthalenesulfonate condensed with formaldehyde, 2 parts by weight
(3) Silicone oil, 0.2 parts by weight
(4) Water, 47.8 parts by weight
The above ingredients are evenly mixed and pulverized to obtain a liquid concentrate. Furthermore,
(5) Sodium polycarboxylate, 5 parts by weight and
(6) Anhydrous sodium sulfate, 42.8 parts by weight
are added thereto and evenly mixed. The mixture is granulated and dried to obtain a water dispersible granule.

Formulation Example 6

(1) Invention Compound, 5 parts by weight
(2) Polyoxyethylene octylphenyl ether, 1 part by weight
(3) Polyoxyethylene alkyl ether phosphate, 0.1 part by weight
(4) Particulate calcium carbonate, 93.9 parts by weight
(1) to (3) are evenly mixed beforehand, and this mixture is diluted with an adequate amount of acetone. Thereafter, the diluted mixture is sprayed on (4) and the acetone is removed to obtain granules.

Formulation Example 7

(1) Invention Compound, 2.5 parts by weight
(2) N,N-dimethylacetamide, 2.5 parts by weight
(3) Soybean oil, 95.0 parts by weight
The above ingredients are evenly mixed and dissolved to obtain an ultra low volume formulation.

Formulation Example 8

(1) Invention Compound, 10 parts by weight
(2) Diethylene glycol monoethyl ether, 80 parts by weight
(3) Polyoxyethylene alkyl ether, 10 parts by weight
The above ingredients are evenly mixed to obtain a liquid formulation.

While the invention has been described in detail and with reference to specific embodiments thereof, it will be apparent to one skill in the art that various changes and modifications can be made therein without departing from the spirit and scope thereof. All references cited herein are incorporated in their entirety. This application is based on Japanese patent application No. 2012-280207 filed on Dec. 21, 2012, Japanese patent application No. 2013-162860 filed on Aug. 6, 2013 and Japanese patent application No. 2013-212795 filed on Oct. 10, 2013, the entire contents of which are incorporated hereinto by reference.

The invention claimed is:

1. A compound represented by general formula (I):

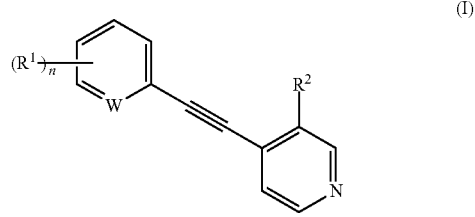

wherein
$R^1$ is a halogen atom, an amino group, a hydroxyl group, a mercapto group, a cyano group, a nitro group, a (C1-C6)alkyl group, a (C2-C6)alkenyl group, a (C2-C6)alkynyl group, a (C3-C6)cycloalkyl group, a (C1-C6)haloalkyl group, a (C1-C6)alkoxy group, a (C2-C6) alkenyloxy group, a (C2-C6)alkynyloxy group, a (C3-C6)cycloalkoxy group, a (C1-C6)haloalkoxy group, a (C1-C6)alkylthio group, a (C2-C6)alkenylthio group, a (C2-C6)alkynylthio group, a (C3-C6)cycloalkylthio group, a (C1-C6)haloalkylthio group, a (C1-C6)alkylamino group, a (C2-C6)alkenylamino group, a (C2-C6)alkynylamino group, a di(C1-C6)alkylamino group, a di(C2-C6)alkenylamino group, a di(C2-C6) alkynylamino group, a (C1-C6)alkylsulfinyl group, a (C2-C6)alkenylsulfinyl group, a (C2-C6)alkynylsulfinyl group, a (C3-C6)cycloalkylsulfinyl group, a (C1-C6)haloalkylsulfinyl group, a (C1-C6)alkylsulfonyl group, a (C2-C6)alkenylsulfonyl group, a (C2-C6)alkynylsulfonyl group, a carboxyl group, a (C1-C6)alkylcarbonyl group, a (C1-C6)alkoxycarbonyl group, a (C1-C6)alkylaminocarbonyl group, a di(C1-C6)alkylaminocarbonyl group, a (C1-C6)alkylcarbonyloxy group, a (C1-C6)alkylcarbonylamino group, or a (C1-C6)alkylcarbonyl(C1-C6)alkylamino group;

$R^2$ is a halogen atom, a hydroxyl group, a mercapto group, a nitro group, a (C1-C6)alkyl group, a (C2-C6)alkenyl group, a (C2-C6)alkynyl group, a (C1-C6)haloalkyl group, a (C1-C6)alkoxy group, a (C2-C6)alkenyloxy group, a (C2-C6)alkynyloxy group, a (C1-C6)alkylthio group, a (C2-C6)alkenylthio group, a (C2-C6)alkynylthio group, a (C1-C6)alkylamino group, a (C2-C6)alkenylamino group, a (C2-C6)alkynylamino group, a di(C1-C6)alkylamino group, a di(C2-C6)alkenylamino group, a di(C2-C6)alkynylamino group, a (C1-C6)alkylsulfinyl group, a (C2-C6)alkenylsulfinyl group, a (C2-C6)alkynylsulfinyl group, a (C1-C6)alkylsulfonyl group, a (C2-C6)alkenylsulfonyl group, a (C2-C6)alkynylsulfonyl group, a (C1-C6)alkyloxy(C1-C6)alkyl group, a (C1-C6)alkylthio(C1-C6)alkyl group, a (C1-C6)alkylamino(C1-C6)alkyl group, a di(C1-C6)alkylamino(C1-C6)alkyl group, a hydroxyl(C1-C6)alkyl group, a carboxyl group, a (C1-C6)alkylcarbonyl group, a (C1-C6)alkylaminocarbonyl group, a di(C1-C6)alkylaminocarbonyl group, a (C1-C6)alkylcarbonyloxy group, a (C1-C6)alkylcarbonylthio group, a (C1-C6)alkylcarbonylamino group, or a di(C1-C6) alkylcarbonylamino group; W is CH or a nitrogen atom; n is an integer of 1-4; when n is 2 or larger, the $R^1$ moieties may be the same or different; and when $R^2$ is a (C1-C6)alkyl group, no R1 moiety substitutes at the ortho position;

or a salt thereof.

2. A pest control agent which comprises the compound or salt thereof according to claim 1 as an active ingredient.

3. A pest control agent for agricultural or horticultural use which comprises the compound or salt thereof according to claim 1 as an active ingredient.

4. An insecticide, miticide, nematicide, or soil pesticide which comprises the compound or salt thereof according to claim 1 as an active ingredient.

5. An insecticide or miticide which comprises the compound or salt thereof according to claim 1 as an active ingredient.

6. An agent for killing animal parasites, comprising the compound or salt thereof according to claim 1 as an active ingredient.

7. A method for controlling a pest, comprising applying the compound or salt thereof according to claim 1 in an effective amount.

* * * * *